(12) United States Patent
Boutillette et al.

(10) Patent No.: US 8,197,400 B2
(45) Date of Patent: Jun. 12, 2012

(54) SELECTIVELY ROTATABLE SHAFT COUPLER

(75) Inventors: Michael P. Boutillette, Watertown, MA (US); Peter L. Dayton, Brookline, MA (US); Dennis R. Boulais, Danielson, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1239 days.

(21) Appl. No.: 11/238,153

(22) Filed: Sep. 28, 2005

(65) Prior Publication Data

US 2006/0111613 A1    May 25, 2006

Related U.S. Application Data

(63) Continuation-in-part of application No. 10/955,960, filed on Sep. 30, 2004, now Pat. No. 7,241,263.

(51) Int. Cl.
*A61B 1/00* (2006.01)
*F16L 27/00* (2006.01)

(52) U.S. Cl. ............... 600/137; 600/136; 285/145.2; 285/147.1

(58) Field of Classification Search ............. 285/50, 285/272, 121.6, 124.2, 145.2, 147.1, 282; 600/136, 137, 127–130, 132, 141–142
See application file for complete search history.

(56) References Cited

U.S. PATENT DOCUMENTS

| | | |
|---|---|---|
| 3,266,059 A | 8/1966 | Stelle |
| 3,470,876 A | 10/1969 | Barchilon |
| 3,572,325 A | 3/1971 | Bazell et al. |
| 3,581,738 A | 6/1971 | Moore |
| 3,692,338 A * | 9/1972 | Nick ............................. 285/272 |
| 4,060,264 A * | 11/1977 | Gajajiva ................... 285/148.19 |
| 4,108,211 A | 8/1978 | Tanaka |
| 4,286,585 A | 9/1981 | Ogawa |
| 4,294,162 A | 10/1981 | Fowler et al. |
| 4,315,309 A | 2/1982 | Coli |
| 4,351,323 A | 9/1982 | Ouchi et al. |
| 4,425,113 A | 1/1984 | Bilstad |
| 4,432,349 A | 2/1984 | Oshiro |
| 4,471,766 A | 9/1984 | Terayama |
| 4,473,841 A | 9/1984 | Murakoshi et al. |
| 4,488,039 A | 12/1984 | Sato et al. |
| 4,491,865 A | 1/1985 | Danna et al. |
| 4,495,134 A | 1/1985 | Ouchi et al. |
| 4,499,895 A | 2/1985 | Takayama |
| 4,513,235 A | 4/1985 | Acklam et al. |
| 4,515,444 A | 5/1985 | Prescott et al. |

(Continued)

FOREIGN PATENT DOCUMENTS

EP    0 689 851 A1    1/1996

(Continued)

*Primary Examiner* — Matthew J Kasztejna
*Assistant Examiner* — Ryan Henderson
(74) *Attorney, Agent, or Firm* — Finnegan, Henderson, Farabow, Garrett & Dunner, LLP

(57) ABSTRACT

The present invention is a system for dissipating loops in an elongated medical device having one end secured to an anchor point, such as a housing. The system includes a selectively rotatable shaft coupler that connects a shaft to the anchor point that allows a limited amount of shaft rotation during use, but which sets a restriction on the maximum amount of shaft rotation. In another embodiment, the invention provides a shaft coupling system for connecting a proximal end of an endoscope shaft to an object without the use of adhesives or fasteners. In another embodiment, the invention provides a rotatable shaft coupling system for rotatably coupling a first and second shaft segment.

17 Claims, 15 Drawing Sheets

U.S. PATENT DOCUMENTS

| | | | |
|---|---|---|---|
| 4,516,063 A | 5/1985 | Kaye et al. |
| 4,519,391 A | 5/1985 | Murakoshi |
| 4,559,928 A | 12/1985 | Takayama |
| 4,573,450 A | 3/1986 | Arakawa |
| 4,576,144 A | 3/1986 | Ishii |
| 4,580,210 A | 4/1986 | Nordstrom |
| 4,586,923 A | 5/1986 | Gould et al. |
| 4,615,330 A | 10/1986 | Nagasaki et al. |
| 4,616,630 A | 10/1986 | Arakawa |
| 4,617,915 A | 10/1986 | Arakawa |
| 4,621,618 A | 11/1986 | Omagari et al. |
| 4,625,714 A | 12/1986 | Toyota |
| 4,631,582 A | 12/1986 | Nagasaki et al. |
| 4,633,303 A | 12/1986 | Nagasaki et al. |
| 4,633,304 A | 12/1986 | Nagasaki |
| 4,643,170 A | 2/1987 | Miyazaki et al. |
| 4,646,723 A | 3/1987 | Arakawa |
| 4,649,904 A | 3/1987 | Krauter et al. |
| 4,651,202 A | 3/1987 | Arakawa |
| 4,652,093 A | 3/1987 | Stephen et al. |
| 4,652,916 A | 3/1987 | Suzaki et al. |
| 4,654,701 A | 3/1987 | Yabe |
| RE32,421 E | 5/1987 | Hattori |
| 4,662,725 A | 5/1987 | Nisioka |
| 4,663,657 A | 5/1987 | Nagasaki et al. |
| 4,667,655 A | 5/1987 | Ogiu et al. |
| 4,674,844 A | 6/1987 | Nishioka et al. |
| 4,686,963 A | 8/1987 | Cohen et al. |
| 4,697,210 A | 9/1987 | Toyota et al. |
| 4,700,693 A | 10/1987 | Lia et al. |
| 4,714,075 A | 12/1987 | Krauter et al. |
| 4,716,457 A | 12/1987 | Matsuo |
| 4,719,508 A | 1/1988 | Sasaki et al. |
| 4,727,417 A | 2/1988 | Kanno et al. |
| 4,727,418 A | 2/1988 | Kato et al. |
| 4,745,470 A | 5/1988 | Yabe et al. |
| 4,745,471 A | 5/1988 | Takamura et al. |
| 4,746,974 A | 5/1988 | Matsuo |
| 4,748,970 A | 6/1988 | Nakajima |
| 4,755,029 A | 7/1988 | Okobe |
| 4,762,119 A | 8/1988 | Allred et al. |
| 4,765,312 A | 8/1988 | Sasa et al. |
| 4,766,489 A | 8/1988 | Kato |
| 4,787,369 A | 11/1988 | Allred et al. |
| 4,790,294 A | 12/1988 | Allred et al. |
| 4,794,913 A | 1/1989 | Shimonaka et al. |
| 4,796,607 A | 1/1989 | Allred et al. |
| 4,800,869 A | 1/1989 | Nakajima |
| 4,805,596 A | 2/1989 | Hatori |
| 4,806,011 A | 2/1989 | Bettinger |
| 4,819,065 A | 4/1989 | Eino |
| 4,819,077 A | 4/1989 | Kikuchi et al. |
| 4,821,116 A | 4/1989 | Nagasaki et al. |
| 4,824,225 A | 4/1989 | Nishioka |
| 4,831,437 A | 5/1989 | Nishioka et al. |
| 4,836,187 A | 6/1989 | Iwakoshi et al. |
| 4,844,052 A | 7/1989 | Iwakoshi et al. |
| 4,844,071 A | 7/1989 | Chen et al. |
| 4,845,553 A | 7/1989 | Konomura et al. |
| 4,845,555 A | 7/1989 | Yabe et al. |
| 4,847,694 A | 7/1989 | Nishihara |
| 4,853,772 A | 8/1989 | Kikuchi |
| 4,860,731 A | 8/1989 | Matsuura |
| 4,867,546 A | 9/1989 | Nishioka et al. |
| 4,868,647 A | 9/1989 | Uehara et al. |
| 4,869,237 A | 9/1989 | Eino et al. |
| 4,873,965 A | 10/1989 | Danieli |
| 4,875,468 A | 10/1989 | Krauter et al. |
| 4,877,314 A | 10/1989 | Kanamori |
| 4,882,623 A | 11/1989 | Uchikubo |
| 4,884,134 A | 11/1989 | Tsuji et al. |
| 4,885,634 A | 12/1989 | Yabe |
| 4,890,159 A | 12/1989 | Ogiu |
| 4,894,715 A | 1/1990 | Uchikubo et al. |
| 4,895,431 A | 1/1990 | Tsujiuchi et al. |
| 4,899,731 A | 2/1990 | Takayama et al. |
| 4,899,732 A | 2/1990 | Cohen |
| 4,899,787 A | 2/1990 | Ouchi et al. |
| 4,905,666 A | 3/1990 | Fukuda |
| 4,918,521 A | 4/1990 | Yabe et al. |
| 4,919,112 A | 4/1990 | Siegmund |
| 4,919,114 A | 4/1990 | Miyazaki |
| 4,920,980 A | 5/1990 | Jackowski |
| 4,928,172 A | 5/1990 | Uehara et al. |
| 4,931,867 A | 6/1990 | Kikuchi |
| 4,941,454 A | 7/1990 | Wood et al. |
| 4,941,456 A | 7/1990 | Wood et al. |
| 4,951,134 A | 8/1990 | Nakasima et al. |
| 4,951,135 A | 8/1990 | Sasagawa et al. |
| 4,952,040 A | 8/1990 | Igarashi |
| 4,960,127 A | 10/1990 | Noce et al. |
| 4,961,110 A | 10/1990 | Nakamura |
| 4,967,269 A | 10/1990 | Sasagawa et al. |
| 4,971,034 A | 11/1990 | Doi et al. |
| 4,973,311 A | 11/1990 | Iwakoshi et al. |
| 4,979,497 A | 12/1990 | Matsuura et al. |
| 4,982,725 A | 1/1991 | Hibino et al. |
| 4,984,878 A | 1/1991 | Miyano |
| 4,986,642 A | 1/1991 | Yokota et al. |
| 4,987,884 A | 1/1991 | Nishioka et al. |
| 4,989,075 A | 1/1991 | Ito |
| 4,989,581 A | 2/1991 | Tamburrino et al. |
| 4,996,974 A | 3/1991 | Ciarlei |
| 4,996,975 A | 3/1991 | Nakamura |
| 4,998,182 A | 3/1991 | Krauter et al. |
| 5,001,556 A | 3/1991 | Nakamura et al. |
| 5,005,558 A | 4/1991 | Aomori |
| 5,005,957 A | 4/1991 | Kanamori et al. |
| 5,007,408 A | 4/1991 | Ieoka |
| 5,018,509 A | 5/1991 | Suzuki et al. |
| 5,022,382 A | 6/1991 | Ohshoki et al. |
| 5,029,016 A | 7/1991 | Hiyama et al. |
| 5,034,888 A | 7/1991 | Uehara et al. |
| 5,040,069 A | 8/1991 | Matsumoto et al. |
| RE33,689 E | 9/1991 | Nishioka et al. |
| 5,045,935 A | 9/1991 | Kikuchi |
| 5,049,989 A | 9/1991 | Tsuji |
| 5,050,584 A | 9/1991 | Matsuura |
| 5,050,974 A | 9/1991 | Takasugi et al. |
| 5,056,503 A | 10/1991 | Nagasaki |
| 5,061,994 A | 10/1991 | Takahashi |
| 5,068,719 A | 11/1991 | Tsuji |
| 5,081,524 A | 1/1992 | Tsuruoka et al. |
| 5,087,989 A | 2/1992 | Igarashi |
| 5,110,645 A | 5/1992 | Matsumoto et al. |
| 5,111,281 A | 5/1992 | Sekiguchi |
| 5,111,306 A | 5/1992 | Kanno et al. |
| 5,111,804 A | 5/1992 | Funakoshi |
| 5,113,254 A | 5/1992 | Kanno et al. |
| 5,119,238 A | 6/1992 | Igarashi |
| 5,131,393 A | 7/1992 | Ishiguro et al. |
| 5,137,013 A | 8/1992 | Chiba et al. |
| 5,140,265 A | 8/1992 | Sakiyama et al. |
| 5,159,446 A | 10/1992 | Hibino et al. |
| 5,170,775 A | 12/1992 | Tagami |
| 5,172,225 A | 12/1992 | Takahashi et al. |
| 5,174,293 A | 12/1992 | Hagiwara |
| 5,176,629 A | 1/1993 | Kullas et al. |
| 5,191,878 A | 3/1993 | Iida et al. |
| 5,198,931 A | 3/1993 | Igarashi |
| 5,201,908 A | 4/1993 | Jones |
| 5,208,702 A | 5/1993 | Shiraiwa |
| 5,209,220 A | 5/1993 | Hiyama et al. |
| 5,217,002 A | 6/1993 | Katsurada et al. |
| 5,225,958 A | 7/1993 | Nakamura |
| 5,228,356 A | 7/1993 | Chuang |
| 5,243,416 A | 9/1993 | Nakazawa |
| 5,243,967 A | 9/1993 | Hibino |
| 5,257,628 A | 11/1993 | Ishiguro et al. |
| 5,271,381 A | 12/1993 | Ailinger et al. |
| RE34,504 E | 1/1994 | Uehara et al. |
| 5,289,555 A | 2/1994 | Sanso |
| 5,291,010 A | 3/1994 | Tsuji |
| 5,299,559 A | 4/1994 | Bruce et al. |
| 5,311,858 A | 5/1994 | Adair |
| 5,325,845 A | 7/1994 | Adair et al. |
| 5,331,551 A | 7/1994 | Tsuruoka et al. |

| Patent No. | Date | Inventor |
|---|---|---|
| 5,342,299 A | 8/1994 | Snoke et al. |
| 5,347,989 A | 9/1994 | Monroe et al. |
| 5,374,953 A | 12/1994 | Sasaki et al. |
| 5,379,757 A | 1/1995 | Hiyama et al. |
| 5,381,782 A | 1/1995 | DeLaRama et al. |
| 5,383,791 A | 1/1995 | Hirakui et al. |
| 5,390,662 A | 2/1995 | Okada |
| 5,400,769 A | 3/1995 | Tanii et al. |
| 5,402,768 A | 4/1995 | Adair |
| 5,402,769 A | 4/1995 | Tsuji |
| 5,406,983 A * | 4/1995 | Chambers et al. ............ 138/109 |
| 5,409,485 A | 4/1995 | Suda |
| 5,412,478 A | 5/1995 | Ishihara et al. |
| 5,418,649 A | 5/1995 | Igarashi |
| 5,420,644 A | 5/1995 | Watanabe |
| 5,431,645 A | 7/1995 | Smith et al. |
| 5,434,615 A | 7/1995 | Matsumoto |
| 5,436,640 A | 7/1995 | Reeves |
| 5,436,767 A | 7/1995 | Suzuki et al. |
| 5,440,341 A | 8/1995 | Suzuki et al. |
| 5,464,007 A | 11/1995 | Krauter et al. |
| 5,469,840 A | 11/1995 | Tanii et al. |
| 5,473,235 A | 12/1995 | Lance et al. |
| 5,482,029 A | 1/1996 | Sekiguchi et al. |
| 5,484,407 A | 1/1996 | Osypka |
| 5,485,316 A | 1/1996 | Mori et al. |
| 5,496,260 A | 3/1996 | Krauter et al. |
| 5,515,449 A | 5/1996 | Tsuruoka et al. |
| 5,518,501 A | 5/1996 | Oneda et al. |
| 5,543,831 A | 8/1996 | Tsuji et al. |
| 5,569,158 A | 10/1996 | Suzuki et al. |
| 5,569,159 A | 10/1996 | Anderson et al. |
| 5,586,262 A | 12/1996 | Komatsu et al. |
| 5,589,854 A | 12/1996 | Tsai |
| 5,591,202 A | 1/1997 | Slater et al. |
| 5,608,451 A | 3/1997 | Konno et al. |
| 5,619,380 A | 4/1997 | Ogasawara et al. |
| 5,621,830 A | 4/1997 | Lucey et al. |
| 5,622,528 A | 4/1997 | Hamano et al. |
| 5,631,695 A | 5/1997 | Nakamura et al. |
| 5,633,203 A | 5/1997 | Adair |
| 5,643,203 A | 7/1997 | Beiser et al. |
| 5,645,075 A | 7/1997 | Palmer et al. |
| 5,647,840 A | 7/1997 | D'Amelio et al. |
| 5,658,238 A | 8/1997 | Suzuki et al. |
| 5,667,477 A | 9/1997 | Segawa |
| 5,674,182 A | 10/1997 | Suzuki et al. |
| 5,674,197 A | 10/1997 | van Muiden et al. |
| 5,685,823 A | 11/1997 | Ito et al. |
| 5,685,825 A | 11/1997 | Takase et al. |
| 5,691,853 A | 11/1997 | Miyano |
| 5,695,450 A | 12/1997 | Yabe et al. |
| 5,698,866 A | 12/1997 | Doiron et al. |
| 5,702,349 A | 12/1997 | Morizumi |
| 5,703,724 A | 12/1997 | Miyano |
| 5,704,371 A | 1/1998 | Shepard |
| 5,704,896 A | 1/1998 | Fukunishi et al. |
| 5,707,340 A | 1/1998 | Hipp et al. |
| 5,708,482 A | 1/1998 | Takahashi et al. |
| 5,721,566 A | 2/1998 | Rosenberg et al. |
| 5,724,068 A | 3/1998 | Sanchez et al. |
| 5,728,045 A | 3/1998 | Komi |
| 5,739,811 A | 4/1998 | Rosenberg et al. |
| 5,740,801 A | 4/1998 | Branson |
| 5,746,696 A | 5/1998 | Kondo |
| 5,764,809 A | 6/1998 | Nomami et al. |
| 5,767,839 A | 6/1998 | Rosenberg |
| 5,781,172 A | 7/1998 | Engel et al. |
| 5,788,714 A | 8/1998 | Ouchi |
| 5,789,047 A | 8/1998 | Sasaki et al. |
| 5,793,539 A | 8/1998 | Konno et al. |
| 5,805,140 A | 9/1998 | Rosenberg et al. |
| 5,810,715 A | 9/1998 | Moriyama |
| 5,812,983 A | 9/1998 | Kumagai |
| 5,819,736 A | 10/1998 | Avny et al. |
| 5,820,591 A | 10/1998 | Thompson et al. |
| 5,821,466 A | 10/1998 | Clark et al. |
| 5,821,920 A | 10/1998 | Rosenberg et al. |
| 5,823,948 A | 10/1998 | Ross, Jr. et al. |
| 5,827,186 A | 10/1998 | Chen et al. |
| 5,827,190 A | 10/1998 | Palcic et al. |
| 5,828,197 A | 10/1998 | Martin et al. |
| 5,828,363 A | 10/1998 | Yaniger et al. |
| 5,830,124 A | 11/1998 | Suzuki et al. |
| 5,830,128 A | 11/1998 | Tanaka |
| 5,836,869 A | 11/1998 | Kudo et al. |
| 5,837,023 A | 11/1998 | Koike et al. |
| 5,837,083 A * | 11/1998 | Booth .......................... 156/158 |
| 5,840,014 A | 11/1998 | Miyano et al. |
| 5,841,126 A | 11/1998 | Fossum et al. |
| 5,843,000 A | 12/1998 | Nishioka et al. |
| 5,846,183 A | 12/1998 | Chilcoat |
| 5,855,560 A | 1/1999 | Idaomi et al. |
| 5,857,963 A | 1/1999 | Pelchy et al. |
| 5,865,724 A | 2/1999 | Palmer et al. |
| 5,868,664 A | 2/1999 | Speier et al. |
| 5,868,666 A | 2/1999 | Okada et al. |
| 5,873,816 A | 2/1999 | Kagawa et al. |
| 5,873,866 A | 2/1999 | Kondo et al. |
| 5,876,326 A | 3/1999 | Takamura et al. |
| 5,876,331 A | 3/1999 | Wu et al. |
| 5,876,373 A | 3/1999 | Giba et al. |
| 5,876,427 A | 3/1999 | Chen et al. |
| 5,877,819 A | 3/1999 | Branson |
| 5,879,284 A | 3/1999 | Tsujita |
| 5,880,714 A | 3/1999 | Rosenberg et al. |
| 5,882,293 A | 3/1999 | Ouchi |
| 5,882,339 A | 3/1999 | Beiser et al. |
| 5,889,670 A | 3/1999 | Schuler et al. |
| 5,889,672 A | 3/1999 | Schuler et al. |
| 5,892,630 A | 4/1999 | Broome |
| 5,895,350 A | 4/1999 | Hori |
| 5,897,507 A | 4/1999 | Kortenbach et al. |
| 5,897,525 A | 4/1999 | Dey et al. |
| 5,907,487 A | 5/1999 | Rosenberg et al. |
| 5,923,018 A | 7/1999 | Kameda et al. |
| 5,928,136 A | 7/1999 | Barry |
| 5,929,607 A | 7/1999 | Rosenberg et al. |
| 5,929,846 A | 7/1999 | Rosenberg et al. |
| 5,929,900 A | 7/1999 | Yamanaka |
| 5,929,901 A | 7/1999 | Adair et al. |
| 5,931,833 A | 8/1999 | Silverstein |
| 5,933,809 A | 8/1999 | Hunt et al. |
| 5,935,085 A | 8/1999 | Welsh et al. |
| 5,936,778 A | 8/1999 | Miyano et al. |
| 5,941,817 A | 8/1999 | Crawford |
| 5,950,168 A | 9/1999 | Simborg et al. |
| 5,951,462 A | 9/1999 | Yamanaka |
| 5,956,416 A | 9/1999 | Tsuruoka et al. |
| 5,956,689 A | 9/1999 | Everhart |
| 5,956,690 A | 9/1999 | Haggerson et al. |
| 5,959,613 A | 9/1999 | Rosenberg et al. |
| 5,976,070 A | 11/1999 | Ono et al. |
| 5,976,074 A | 11/1999 | Moriyama |
| 5,980,454 A | 11/1999 | Broome |
| 5,980,468 A | 11/1999 | Zimmon |
| 5,986,693 A | 11/1999 | Adair et al. |
| 5,991,729 A | 11/1999 | Barry et al. |
| 5,991,730 A | 11/1999 | Lubin et al. |
| 5,999,168 A | 12/1999 | Rosenberg et al. |
| 6,002,425 A | 12/1999 | Yamanaka et al. |
| 6,007,531 A | 12/1999 | Snoke et al. |
| 6,014,630 A | 1/2000 | Jeacock et al. |
| 6,015,088 A | 1/2000 | Parker et al. |
| 6,017,322 A | 1/2000 | Snoke et al. |
| 6,020,875 A | 2/2000 | Moore et al. |
| 6,020,876 A | 2/2000 | Rosenberg et al. |
| 6,026,363 A | 2/2000 | Shepard |
| 6,030,360 A | 2/2000 | Biggs |
| 6,032,120 A | 2/2000 | Rock et al. |
| 6,039,728 A | 3/2000 | Berlien et al. |
| 6,043,839 A | 3/2000 | Adair et al. |
| 6,050,718 A | 4/2000 | Schena et al. |
| 6,057,828 A | 5/2000 | Schena et al. |
| 6,059,719 A | 5/2000 | Yamamoto et al. |
| 6,061,004 A | 5/2000 | Rosenberg |
| 6,063,035 A | 5/2000 | Sakamoto |
| 6,067,077 A | 5/2000 | Martin et al. |

| | | | |
|---|---|---|---|
| 6,071,248 A | 6/2000 | Zimmon | |
| 6,075,555 A | 6/2000 | Street | |
| 6,078,308 A | 6/2000 | Rosenberg et al. | |
| 6,078,353 A | 6/2000 | Yamanaka et al. | |
| 6,078,876 A | 6/2000 | Rosenberg et al. | |
| 6,080,104 A | 6/2000 | Ozawa et al. | |
| 6,081,809 A | 6/2000 | Kumagai | |
| 6,083,152 A | 7/2000 | Strong | |
| 6,083,170 A | 7/2000 | Ben-Haim | |
| 6,095,971 A | 8/2000 | Takahashi | |
| 6,099,465 A | 8/2000 | Inoue | |
| 6,100,874 A | 8/2000 | Schena et al. | |
| 6,104,382 A | 8/2000 | Martin et al. | |
| 6,120,435 A | 9/2000 | Eino | |
| 6,125,337 A | 9/2000 | Rosenberg et al. | |
| 6,128,006 A | 10/2000 | Rosenberg et al. | |
| 6,132,369 A | 10/2000 | Takahashi | |
| 6,134,056 A | 10/2000 | Nakamura | |
| 6,134,506 A | 10/2000 | Rosenberg et al. | |
| 6,135,946 A | 10/2000 | Konen et al. | |
| 6,139,508 A | 10/2000 | Simpson et al. | |
| 6,141,037 A | 10/2000 | Upton et al. | |
| 6,142,956 A | 11/2000 | Kortenbach et al. | |
| 6,146,355 A | 11/2000 | Biggs | |
| 6,149,607 A | 11/2000 | Simpson et al. | |
| 6,152,877 A | 11/2000 | Masters | |
| 6,154,198 A | 11/2000 | Rosenberg | |
| 6,154,248 A | 11/2000 | Ozawa et al. | |
| 6,155,988 A | 12/2000 | Peters | |
| 6,181,481 B1 | 1/2001 | Yamamoto et al. | |
| 6,184,922 B1 | 2/2001 | Saito et al. | |
| 6,193,714 B1 | 2/2001 | McGaffigan et al. | |
| 6,195,592 B1 | 2/2001 | Schuler et al. | |
| 6,203,493 B1 | 3/2001 | Ben-Haim | |
| 6,206,824 B1 | 3/2001 | Ohara et al. | |
| 6,211,904 B1 | 4/2001 | Adair | |
| 6,216,104 B1 | 4/2001 | Moshfeghi et al. | |
| 6,219,091 B1 | 4/2001 | Yamanaka et al. | |
| 6,221,070 B1 | 4/2001 | Tu et al. | |
| 6,241,668 B1 | 6/2001 | Herzog | |
| 6,260,994 B1 | 7/2001 | Matsumoto et al. | |
| 6,272,470 B1 | 8/2001 | Teshima | |
| 6,275,255 B1 | 8/2001 | Adair et al. | |
| 6,283,960 B1 | 9/2001 | Ashley | |
| 6,295,082 B1 | 9/2001 | Dowdy et al. | |
| 6,299,625 B1 | 10/2001 | Bacher | |
| 6,309,347 B1 | 10/2001 | Takahashi et al. | |
| 6,310,642 B1 | 10/2001 | Adair et al. | |
| 6,319,196 B1 | 11/2001 | Minami | |
| 6,319,197 B1 | 11/2001 | Tsuji et al. | |
| 6,334,844 B1 | 1/2002 | Akiba | |
| 6,346,075 B1 | 2/2002 | Arai et al. | |
| 6,366,799 B1 | 4/2002 | Acker et al. | |
| 6,381,029 B1 | 4/2002 | Tipirneni | |
| 6,398,724 B1 | 6/2002 | May et al. | |
| 6,413,207 B1 | 7/2002 | Minami | |
| 6,421,078 B1 | 7/2002 | Akai et al. | |
| 6,425,535 B1 | 7/2002 | Akiba | |
| 6,425,858 B1 | 7/2002 | Minami | |
| 6,436,032 B1 | 8/2002 | Eto et al. | |
| 6,441,845 B1 | 8/2002 | Matsumoto | |
| 6,447,444 B1 | 9/2002 | Avni et al. | |
| 6,449,006 B1 | 9/2002 | Shipp | |
| 6,453,190 B1 | 9/2002 | Acker et al. | |
| 6,454,162 B1 | 9/2002 | Teller | |
| 6,459,447 B1 | 10/2002 | Okada et al. | |
| 6,468,204 B2 | 10/2002 | Sendai et al. | |
| 6,475,141 B2 | 11/2002 | Abe | |
| 6,478,730 B1 | 11/2002 | Bala et al. | |
| 6,489,987 B1 | 12/2002 | Higuchi et al. | |
| 6,496,827 B2 | 12/2002 | Kozam et al. | |
| 6,498,948 B1 | 12/2002 | Ozawa et al. | |
| 6,503,193 B1 | 1/2003 | Iwasaki et al. | |
| 6,520,908 B1 * | 2/2003 | Ikeda et al. | 600/132 |
| 6,524,234 B2 | 2/2003 | Ouchi | |
| 6,530,882 B1 | 3/2003 | Farkas et al. | |
| 6,533,722 B2 | 3/2003 | Nakashima | |
| 6,540,669 B2 | 4/2003 | Abe et al. | |
| 6,544,194 B1 | 4/2003 | Kortenbach et al. | |
| 6,545,703 B1 | 4/2003 | Takahashi et al. | |
| 6,551,239 B2 | 4/2003 | Renner et al. | |
| 6,558,317 B2 | 5/2003 | Takahashi et al. | |
| 6,561,971 B1 | 5/2003 | Akiba | |
| 6,565,507 B2 | 5/2003 | Kamata et al. | |
| 6,574,629 B1 | 6/2003 | Cooke, Jr. et al. | |
| 6,589,162 B2 | 7/2003 | Nakashima et al. | |
| 6,595,913 B2 | 7/2003 | Takahashi | |
| 6,597,390 B1 | 7/2003 | Higuchi | |
| 6,599,239 B2 | 7/2003 | Hayakawa et al. | |
| 6,602,186 B1 | 8/2003 | Sugimoto et al. | |
| 6,605,035 B2 | 8/2003 | Ando et al. | |
| 6,609,135 B1 | 8/2003 | Omori et al. | |
| 6,611,846 B1 | 8/2003 | Stoodley | |
| 6,614,969 B2 | 9/2003 | Eichelberger et al. | |
| 6,616,601 B2 | 9/2003 | Hayakawa | |
| 6,623,424 B2 | 9/2003 | Hayakawa et al. | |
| 6,638,214 B2 | 10/2003 | Akiba | |
| 6,638,215 B2 | 10/2003 | Kobayashi | |
| 6,641,528 B2 | 11/2003 | Torii | |
| 6,651,669 B1 | 11/2003 | Burnside | |
| 6,656,110 B1 | 12/2003 | Irion et al. | |
| 6,656,112 B2 | 12/2003 | Miyanaga | |
| 6,659,940 B2 | 12/2003 | Adler | |
| 6,663,561 B2 | 12/2003 | Sugimoto et al. | |
| 6,669,629 B2 | 12/2003 | Matsui | |
| 6,673,012 B2 | 1/2004 | Fujii et al. | |
| 6,677,984 B2 | 1/2004 | Kobayashi et al. | |
| 6,678,397 B1 | 1/2004 | Omori et al. | |
| 6,682,479 B1 | 1/2004 | Takahashi et al. | |
| 6,685,631 B2 | 2/2004 | Minami | |
| 6,686,949 B2 | 2/2004 | Kobayashi et al. | |
| 6,690,409 B1 | 2/2004 | Takahashi | |
| 6,690,963 B2 | 2/2004 | Ben-Haim et al. | |
| 6,692,431 B2 | 2/2004 | Kazakevich | |
| 6,697,101 B1 | 2/2004 | Takahashi et al. | |
| 6,699,181 B2 | 3/2004 | Wako | |
| 6,702,737 B2 | 3/2004 | Hinto et al. | |
| 6,711,426 B2 | 3/2004 | Benaron et al. | |
| 6,715,068 B1 | 3/2004 | Abe | |
| 6,716,162 B2 | 4/2004 | Hakamata | |
| 6,728,599 B2 | 4/2004 | Wang et al. | |
| 6,730,018 B2 | 5/2004 | Takase | |
| 6,736,773 B2 | 5/2004 | Wendlandt et al. | |
| 6,743,240 B2 | 6/2004 | Smith et al. | |
| 6,749,559 B1 | 6/2004 | Kraas et al. | |
| 6,749,560 B1 | 6/2004 | Konstorum et al. | |
| 6,749,561 B2 | 6/2004 | Kazakevich | |
| 6,753,905 B1 | 6/2004 | Okada et al. | |
| 6,758,806 B2 | 7/2004 | Kamrava et al. | |
| 6,758,807 B2 | 7/2004 | Minami | |
| 6,758,842 B2 | 7/2004 | Irion et al. | |
| 6,778,208 B1 | 8/2004 | Takeshige et al. | |
| 6,780,151 B2 | 8/2004 | Grabover et al. | |
| 6,785,410 B2 | 8/2004 | Vining et al. | |
| 6,785,593 B2 | 8/2004 | Wang et al. | |
| 6,796,938 B2 | 9/2004 | Sendai | |
| 6,796,939 B1 | 9/2004 | Hirata et al. | |
| 6,798,533 B2 | 9/2004 | Tipirneni | |
| 6,800,056 B2 | 10/2004 | Tartaglia et al. | |
| 6,800,057 B2 | 10/2004 | Tsujita et al. | |
| 6,808,491 B2 | 10/2004 | Kortenbach et al. | |
| 6,824,539 B2 | 11/2004 | Novak | |
| 6,824,548 B2 | 11/2004 | Smith et al. | |
| 6,829,003 B2 | 12/2004 | Takami | |
| 6,830,545 B2 | 12/2004 | Bendall | |
| 6,832,990 B2 | 12/2004 | Kortenbach et al. | |
| 6,840,932 B2 | 1/2005 | Lang et al. | |
| 6,842,196 B1 | 1/2005 | Swift et al. | |
| 6,846,286 B2 | 1/2005 | Suzuki et al. | |
| 6,847,933 B1 | 1/2005 | Hastings | |
| 6,849,043 B2 | 2/2005 | Kondo | |
| 6,850,794 B2 | 2/2005 | Shahidi | |
| 6,855,109 B2 | 2/2005 | Obata et al. | |
| 6,858,004 B1 | 2/2005 | Ozawa et al. | |
| 6,858,014 B2 | 2/2005 | Damarati | |
| 6,860,849 B2 | 3/2005 | Matsushita et al. | |
| 6,863,650 B1 | 3/2005 | Irion | |
| 6,863,661 B2 | 3/2005 | Carrillo et al. | |

| | | |
|---|---|---|
| 6,868,195 B2 | 3/2005 | Fujita |
| 6,871,086 B2 | 3/2005 | Nevo et al. |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayahi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami et al. |
| 6,949,068 B2 | 9/2005 | Taniguchi et al. |
| 6,950,691 B2 | 9/2005 | Uchikubo |
| 6,955,671 B2 | 10/2005 | Uchikubo |
| 7,108,063 B2 * | 9/2006 | Carstensen ............... 166/241.2 |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0193664 A1 | 12/2002 | Ross et al. |
| 2003/0032863 A1 | 2/2003 | Kazakevich |
| 2003/0069897 A1 | 4/2003 | Roy et al. |
| 2003/0078476 A1 * | 4/2003 | Hill ............................. 600/160 |
| 2003/0149338 A1 | 8/2003 | Francois et al. |
| 2003/0181905 A1 | 9/2003 | Long |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Maeda et al. |
| 2004/0073085 A1 | 4/2004 | Ikeda et al. |
| 2004/0147809 A1 | 7/2004 | Kazakevich |
| 2004/0167379 A1 | 8/2004 | Akiba |
| 2004/0249247 A1 | 12/2004 | Iddan |
| 2004/0257608 A1 | 12/2004 | Tipirneni |
| 2005/0197861 A1 | 9/2005 | Omori et al. |
| 2005/0203341 A1 | 9/2005 | Welker et al. |
| 2005/0228697 A1 | 10/2005 | Funahashi |
| 2005/0273084 A1 | 12/2005 | Hinman et al. |
| 2006/0111616 A1 * | 5/2006 | Danitz ........................ 600/142 |

FOREIGN PATENT DOCUMENTS

| | | |
|---|---|---|
| EP | 1 300 883 A2 | 4/2003 |
| JP | 58-78635 A | 5/1983 |
| JP | 05-31071 A | 2/1993 |
| JP | 05-091972 A | 4/1993 |
| JP | 06-105800 | 4/1994 |
| JP | 06-254048 A | 9/1994 |
| JP | 07-8441 A | 1/1995 |
| JP | 10-113330 A | 5/1998 |
| JP | 10-286221 A | 10/1998 |
| JP | 11-216113 A | 8/1999 |
| JP | 3219521 B2 | 8/2001 |
| JP | 2002-102152 A | 4/2002 |
| JP | 2002-177197 A | 6/2002 |
| JP | 2002-185873 A | 6/2002 |
| JP | 2002-253481 A | 9/2002 |
| JP | 3372273 B2 | 11/2002 |
| JP | 2003-75113 A | 3/2003 |
| JP | 3482238 B2 | 10/2003 |
| WO | WO 93/13704 A1 | 7/1993 |
| WO | WO 2004/016310 A2 | 2/2004 |
| WO | WO 2005/023082 A2 | 3/2005 |

* cited by examiner

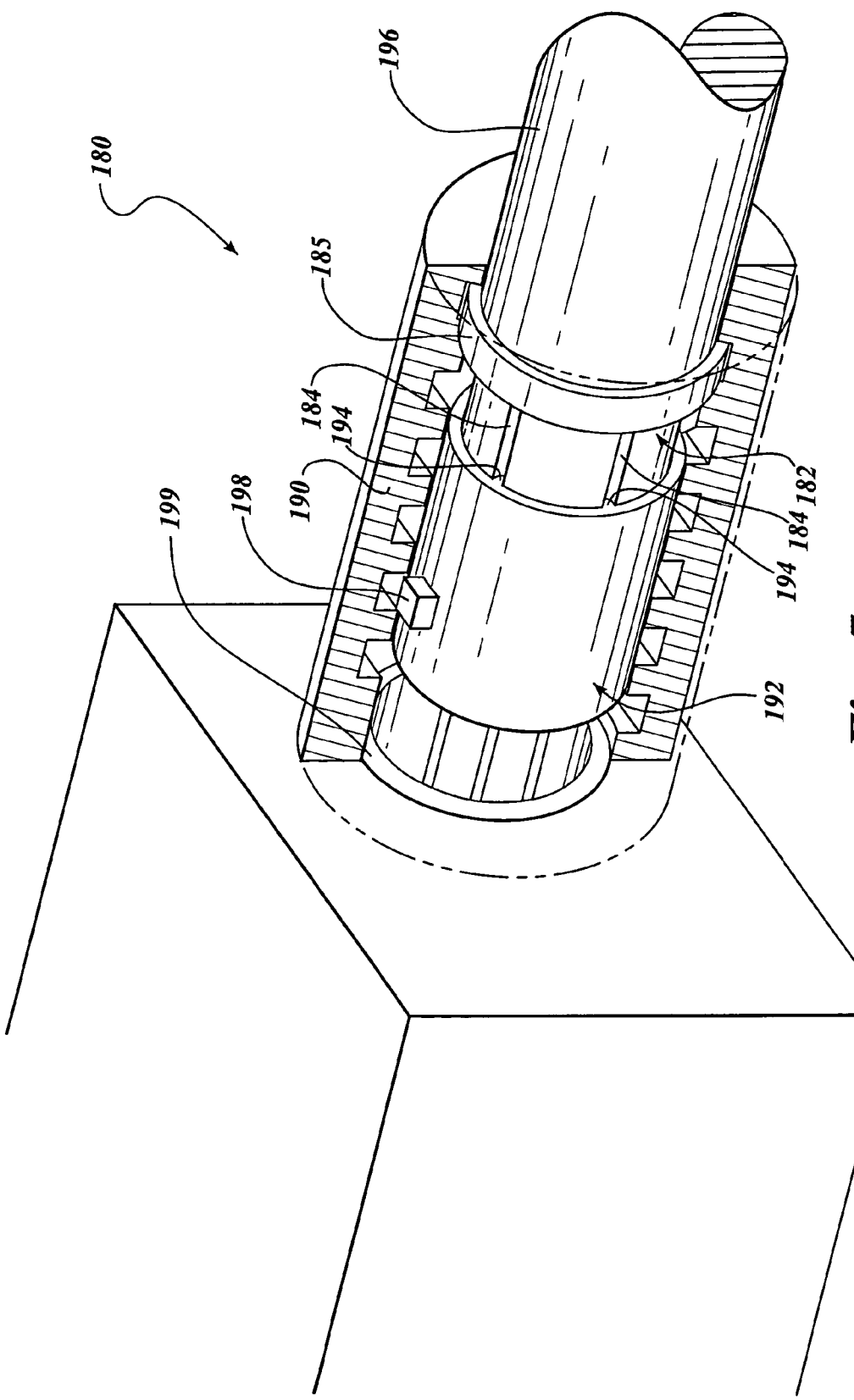

SELECTIVELY ROTATABLE SHAFT COUPLER

CROSS-REFERENCE TO RELATED APPLICATION

This application is a continuation-in-part of U.S. application Ser. No. 10/955,960, filed Sep. 30, 2004, entitled SELECTIVELY ROTATABLE SHAFT COUPLER, the disclosure of which is hereby expressly incorporated by reference and the priority from the filing date of which is hereby claimed under 35 U.S.C. §120.

FIELD OF THE INVENTION

The present invention relates to shaft couplers for medical devices in general and to rotatable shaft couplers in particular.

BACKGROUND OF THE INVENTION

It has become well established that there are major health benefits from regular endoscopic examinations of a patient's internal structures such as the alimentary canals and airways, e.g., the esophagus, stomach, lungs, colon, uterus, urethra, kidney, and other organ systems. Endoscopes are also commonly used to perform surgical, therapeutic, diagnostic or other medical procedures under direct visualization. A conventional imaging endoscope used for such procedures generally includes an illuminating mechanism such as a fiber optic light guide connected to a proximal source of light, and an imaging means such as an imaging light guide to carry an image to a remote camera or eye piece or a miniature video camera within the endoscope itself. In addition, most endoscopes include one or more working channels through which medical devices such as biopsy forceps, snares, fulguration probes and other tools may be passed in order to perform a procedure at a desired location in the patient's body.

In connection with the endoscope, an operator handle is typically provided that allows a user to steer and control the operation of the endoscope. The endoscope is guided through the patient's tract or canal until an opening such as an imaging port at the distal end of the endoscope is proximate to the area of the patient's body which is to be examined or receive treatment. At this point, the endoscope allows other components, such as a catheter, to access the targeted area.

In many endoscopic procedures, the physician or operator needs to rotate an endoscope shaft in order to obtain the desired images, to obtain a desired position of the distal tip, or to perform a desired surgical function (e.g. polyp removal, drainage, and the like). An endoscope shaft with torque transfer characteristics facilitates shaft rotation in the patient's anatomy by allowing the shaft to twist around its central axis. Excessive rotation of the shaft can damage the cables, tubes and electrical wires within the device. On the other hand, an endoscope shaft that is not allowed to rotate relative to the position of the handle at all may loop over itself during clinical use, causing damage to the internal components as well as discomfort to the patient. In a traditional endoscope system, when loops build up in the shaft, the physician typically propagates the loops back into the proximal portion of the shaft to keep the loops out of the physician's way. However, the loops can shorten the proximal shaft. In some cases when there is an excessive amount of looping in the shaft, the physician is forced to disconnect the scope from a console, untwist the proximal shaft, and reconnect the scope.

Low cost, disposable medical devices designated for a single use have become popular for instruments that are difficult to sterilize or clean properly. Single-use, disposable devices are packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction and sterilization. One medical device that has not previously been inexpensive enough to be considered truly disposable is the endoscope, such as a colonoscope, ureteroscope, gastroscope, bronchoscope, duodenoscope, etc. Such a single-use or disposable endoscope is described in U.S. patent application Ser. No. 10/406,149, filed Apr. 1, 2003, and in a U.S. continuation-in-part patent application Ser. No. 10/811,781, filed Mar. 29, 2004, and in a U.S. continuation-in-part patent application Ser. No. 10/956,007, filed Sep. 30, 2004, that are assigned to Scimed Life Systems, Inc., now Boston Scientific Scimed, Inc. and are herein incorporated by reference. In some single-use or disposable medical device systems, the system is configured to reject a medical device that has been previously used. Therefore, when a physician builds up loops in the proximal shaft of a single-use device in such a system, the physician is not able to disconnect and reconnect the shaft to remove the loops. In such a situation, the physician is left with the option of using the device with a shorter working length.

SUMMARY OF THE INVENTION

To address these and other problems, the present invention is a system for dissipating loops in an elongated medical device having one end secured to an anchor point, such as an object, housing, console, etc. In one embodiment, the system includes a selectively rotatable shaft coupler that connects a shaft to a housing that allows a limited amount of shaft rotation during use, but which sets a restriction on the maximum amount of shaft rotation. The rotatable shaft coupler comprises a coupler housing that is secured to an anchor and a shaft adapter that securable to the shaft of medical device, the coupler including means for allowing a limited rotation during use between the shaft adapter and the housing. In one embodiment, the system maintains the effective length of the endoscope shaft during rotation.

In another embodiment, the present invention provides a shaft coupling system for connecting an endoscope shaft to a housing or other structure. The shaft coupling system comprises a housing with a first end adapted to receive a shaft retainer and a shaft retainer comprising a plurality of retention elements capable of securing an end of an endoscope shaft.

In another embodiment, the present invention provides a system for rotatably coupling a first segment of an endoscope shaft to a second segment of an endoscope shaft. The system includes an endoscope shaft and one or more internal components therein, wherein the shaft is formed into first and second segments. A swivel joint having a housing with a first and a second end rotatably connects the ends of the two shaft segments.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 7 illustrates yet another embodiment of a selectively rotatable shaft coupler that maintains the effective length of the endoscope shaft during rotation, in accordance with the present invention;

DETAILED DESCRIPTION OF THE PREFERRED EMBODIMENT

To address the problems associated with excessive endoscope shaft rotation, one aspect of the present invention is a system for rotatably coupling a shaft to an anchor point, such as a housing. The system comprises a selectively rotatable shaft coupler that allows a limited amount of device (e.g., endoscope) shaft rotation during use, but which sets a restriction on the maximum amount of shaft rotation in order to provide increased manipulation of the endoscope while protecting the internal components of the shaft. Although the present invention is described as allowing rotation of an endoscope, it will be appreciated that the invention is useful with catheters, sheaths or other medical devices that are inserted into a patient, wherein selective rotation of a shaft with respect to another part of the device is desired.

In one embodiment, the shaft coupler system of the present invention comprises at least one selectively rotatable shaft adapter that connects an endoscope shaft to a connector that is secured to the device to which the shaft is to be rotatably connected. In one embodiment, the shaft coupler connects a shaft to a device such as a handle, control unit or working channel breakout box, such as described in U.S. patent application Ser. No. 10/811,781, filed Mar. 29, 2004, and in a U.S. continuation-in-part patent application Ser. No. 10/956,007 entitled VIDEO ENDOSCOPE, filed Sep. 30, 2004, that are assigned to Scimed Life Systems Inc., now Boston Scientific Scimed, Inc. In another embodiment, the shaft coupler system is used to join two sections of a shaft together.

Figure 1:
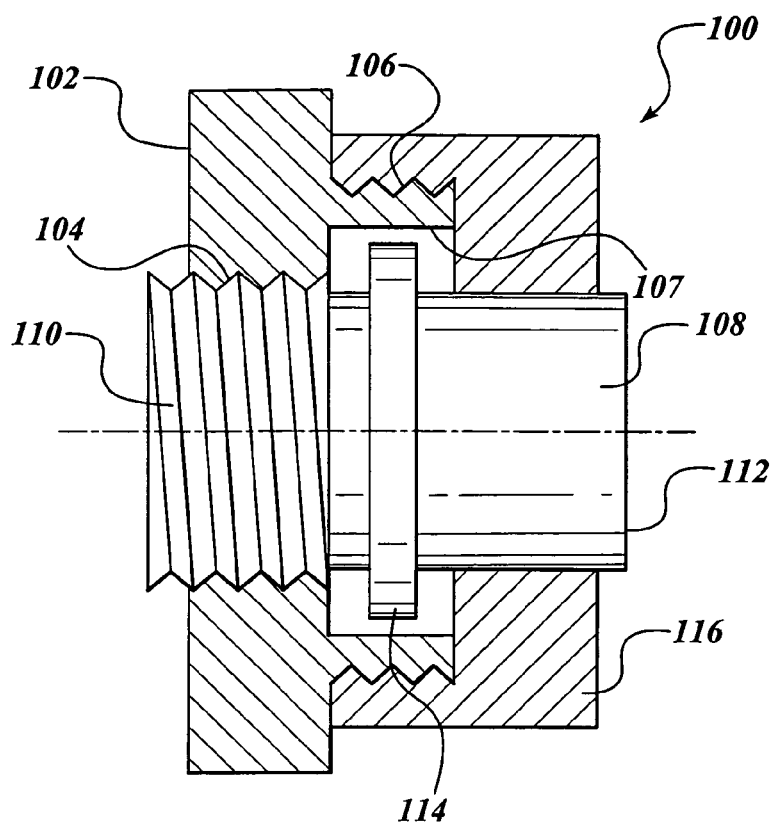
FIG. 1 is a diagram illustrating a selectively rotatable shaft coupler in accordance with one embodiment of the invention.

FIG. 1 illustrates an exemplary embodiment of a selectively rotatable shaft coupler 100 for connecting an endoscope shaft (not shown) to a proximal connector housing 102. In the embodiment shown, the proximal connector housing 102 is rigidly secured to another object to which the endoscope is to be rotatably secured. The proximal connector housing 102 has a threaded bore 104 into which a corresponding threaded end 110 of a shaft adapter 108 is inserted. The proximal connector housing 102 also includes an outwardly extending threaded nipple 106 having a smooth bore 107 therein. The proximal connector housing 102 may be secured to the object by a variety of means such as an adhesive, or with any suitable fastener, or may be integrally formed with the object. The depth of the bore 107 determines the maximum range of endoscope shaft rotation.

A shaft adapter 108 has a first threaded end 110 that is threaded within the connector housing 102 and a second end 112 that is secured to the endoscope shaft (not shown). Between the first and second ends of the shaft adapter 108 is a circular flange 114. A cap 116 is threaded over the adapter 108 and onto the nipple 106 in order to close the flange 114 within the bore 107. The shaft coupler 100, comprising the shaft adapter 108 and the connector housing 102, may be packaged as a preformed unit that can be removably attached to a housing or to any desired object with any suitable connection means.

Figure 2:
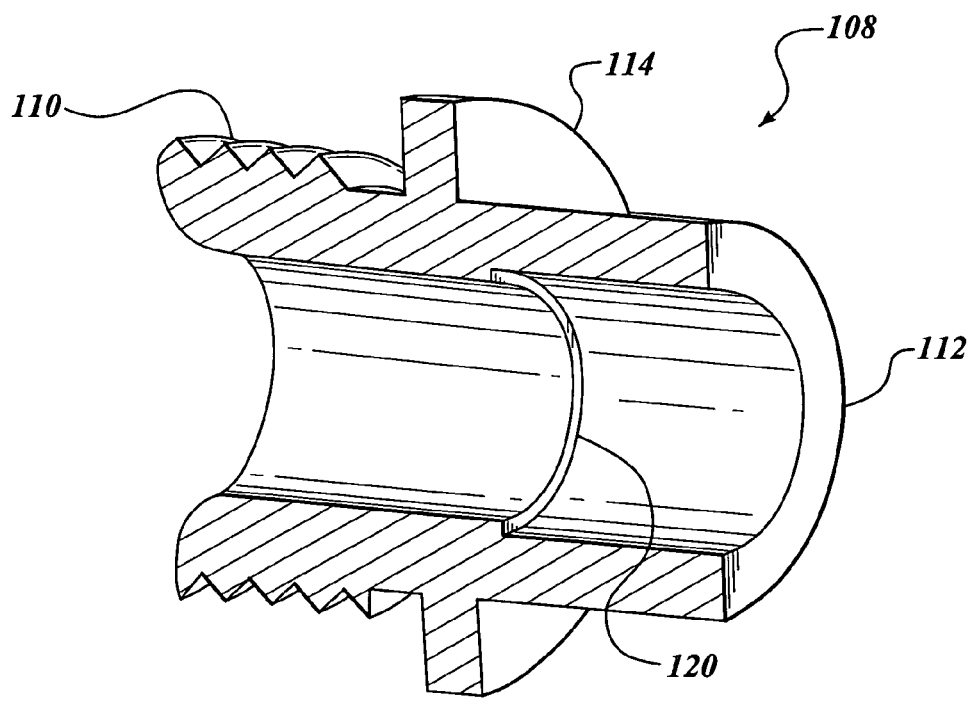
FIG. 2 shows a cross-sectional view of a shaft adapter that is included in the shaft coupler shown in FIG. 1.

FIG. 2 shows a cross-sectional view of the shaft adapter 108. As shown, the shaft adapter 108 has a hollow body with a first end 110 adapted to be threaded with the proximal connector housing 102 and a second end 112 adapted to be secured to the end of an endoscope shaft. As shown, the shaft adapter has a central hollow lumen through which control cables and other elements of the endoscope are passed to allow electrical, irrigation and aspiration connections to extend into the endoscope. A counter-bored detail 120 inside the second end 112 of the shaft adapter 108 receives an end of an endoscope shaft. Alternatively, the second end 112 of the shaft adapter may be sized to fit inside an end of an endoscope shaft and secure the shaft by any suitable means, such as with the use of an adhesive and/or any suitable fastener.

Figure 3A:
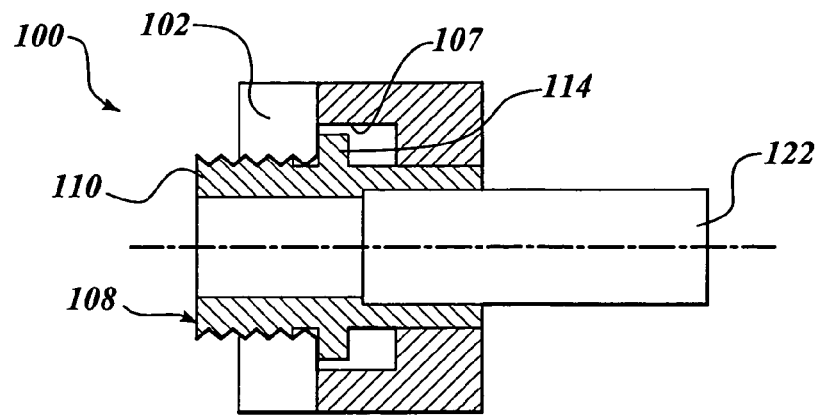
FIG. 3A is a diagram illustrating the selectively rotatable shaft adapter of FIG. 2 shown in a position of maximum rotation in a first direction.
Figure 3B:
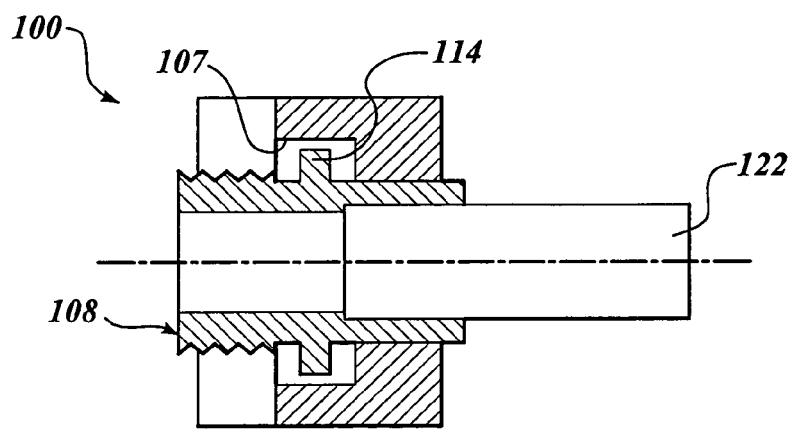
FIG. 3B shows the selectively rotatable shaft adapter of FIG. 2 shown in a position of minimal endoscope shaft rotation.
Figure 3C:
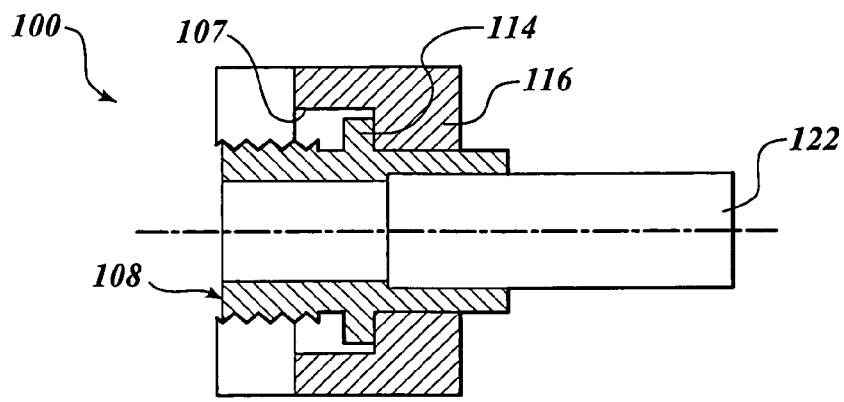
FIG. 3C shows the selectively rotatable shaft adapter of FIG. 2 coupled to an endoscope shaft showing maximum rotation in a second direction.

FIGS. 3A-C illustrate the rotational movement of the shaft adapter 108 in the proximal connector housing 102 when coupled to a rotating endoscope shaft 122. In operation, as shown in FIG. 3A, an end of an endoscope shaft 122 is first secured to an end of the shaft adapter 108. Rotation of the shaft by the physician causes the shaft adapter 108 to rotate along with the endoscope shaft 122. Rotation of the shaft 122 in a first direction (e.g., clockwise) causes axial movement of the shaft adapter 108 within the proximal connector until the flange 114 contacts the bottom of the bore 107 by the threads on the end 110 of the shaft adapter 108. As shown in FIG. 3B, the flange 114 is in an intermediate position in the cylindrical bore 107, indicating a midway rotation of the endoscope shaft 122. Finally, as shown in FIG. 3C, rotation of the shaft in a full counterclockwise direction causes axial movement of the shaft adapter 108 towards the cap 116 until the flange 114 in the bore 107 contacts the interior surface of the cap 116. The depth of the bore 107 and the width of the flange 114 and/or the pitch of the threads that secure the shaft adapter 108 to the proximal connector housing 102, may be adjusted to allow for various amounts of rotational motion of the shaft.

Figure 4:
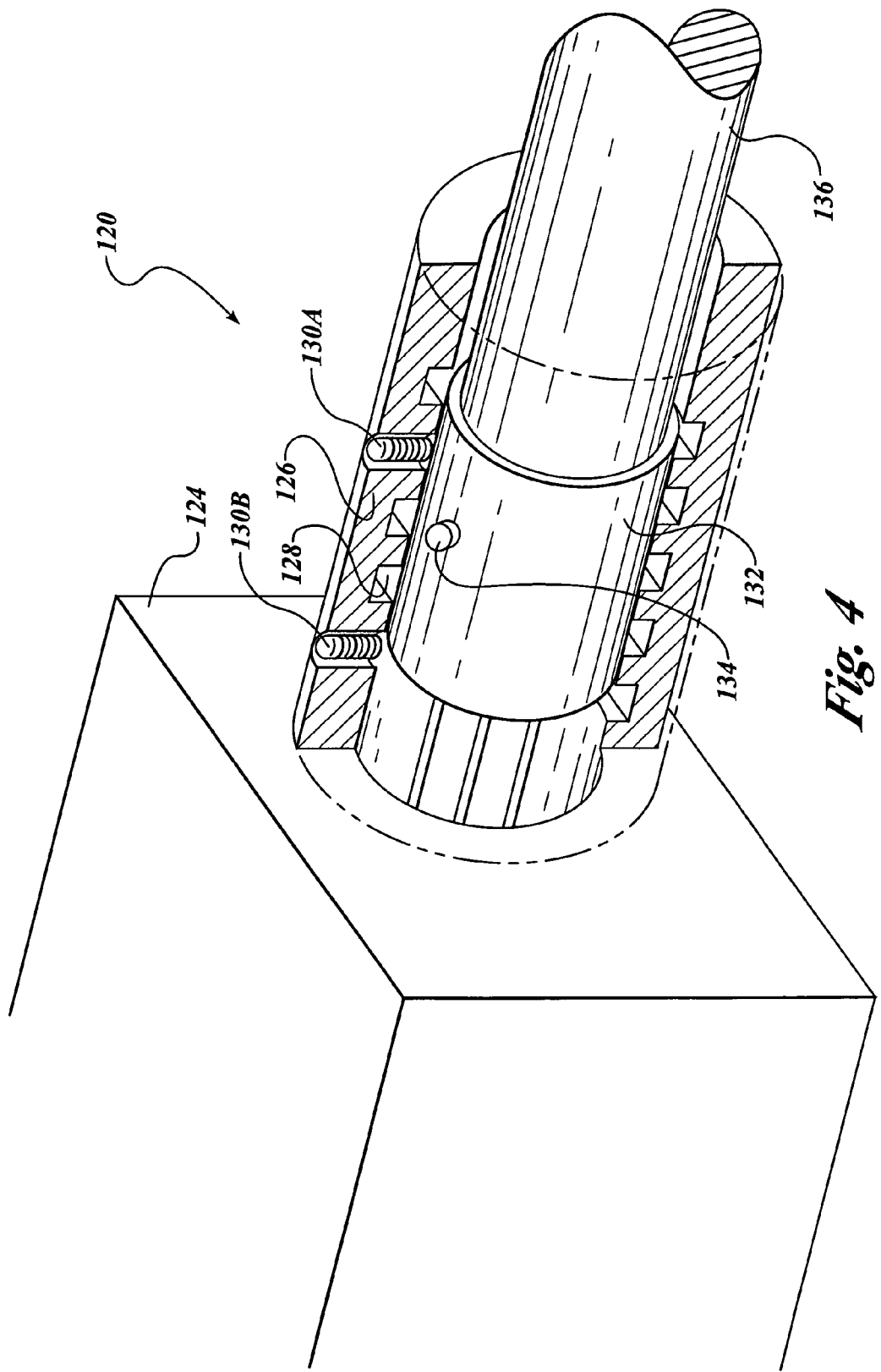
FIG. 4 illustrates another embodiment of a selectively rotatable shaft coupler in accordance with the present invention.

FIG. 4 is a partial cutaway view of another embodiment of a selectively rotatable shaft coupler 120 attached to an anchor point, such as an object 124. As shown, the coupler 120 includes an internally threaded collar 126 that extends from, or is attached to, the object 124. A shaft adapter 132 is secured to an end of an endoscope shaft 136 and an engagement element such as a pin 134 is sized to be received in the threads 128 of the threaded collar 126. In operation, the engagement pin 134, or other equivalent engagement element on the shaft adapter 132, rides in the threads 128 of the threaded collar 126, causing the shaft adapter 132 to move axially in and out of the coupler 120 during rotation of the endoscope shaft 136. To limit rotation of the shaft during use, one or more stop elements 130A, 130B are positioned to extend into the threads 128 of the threaded collar to prevent movement of the engagement pin 134. The location of each of the two stop pins 130A, 130B in the threads and the pitch of the threads determines the range of endoscope shaft rotation.

In some embodiments, the stop elements 130A, 130B may be tightened onto the shaft adapter 132, thereby locking the endoscope shaft 136 into a desired orientation during clinical use. Although the embodiment shown uses two stop pins 130A, 130B, it will be appreciated that the amount of rotation can be determined by limiting the depth of the threads in the collar 126.

Similarly, although the embodiment shown in FIG. 4 is described with reference to stop elements as pins, those of skill in the art will understand that the stop elements may comprise any suitable structure capable of preventing the rotation of the shaft adapter 132 in the collar 126, such as blocks, tabs and the like. Similarly, those of skill in the art will understand that a suitable engagement element is not limited to a pin, but also includes any structure capable of allowing rotation in the collar 126 such as tabs, blocks, a smaller threaded section, and the like.

Figure 5:
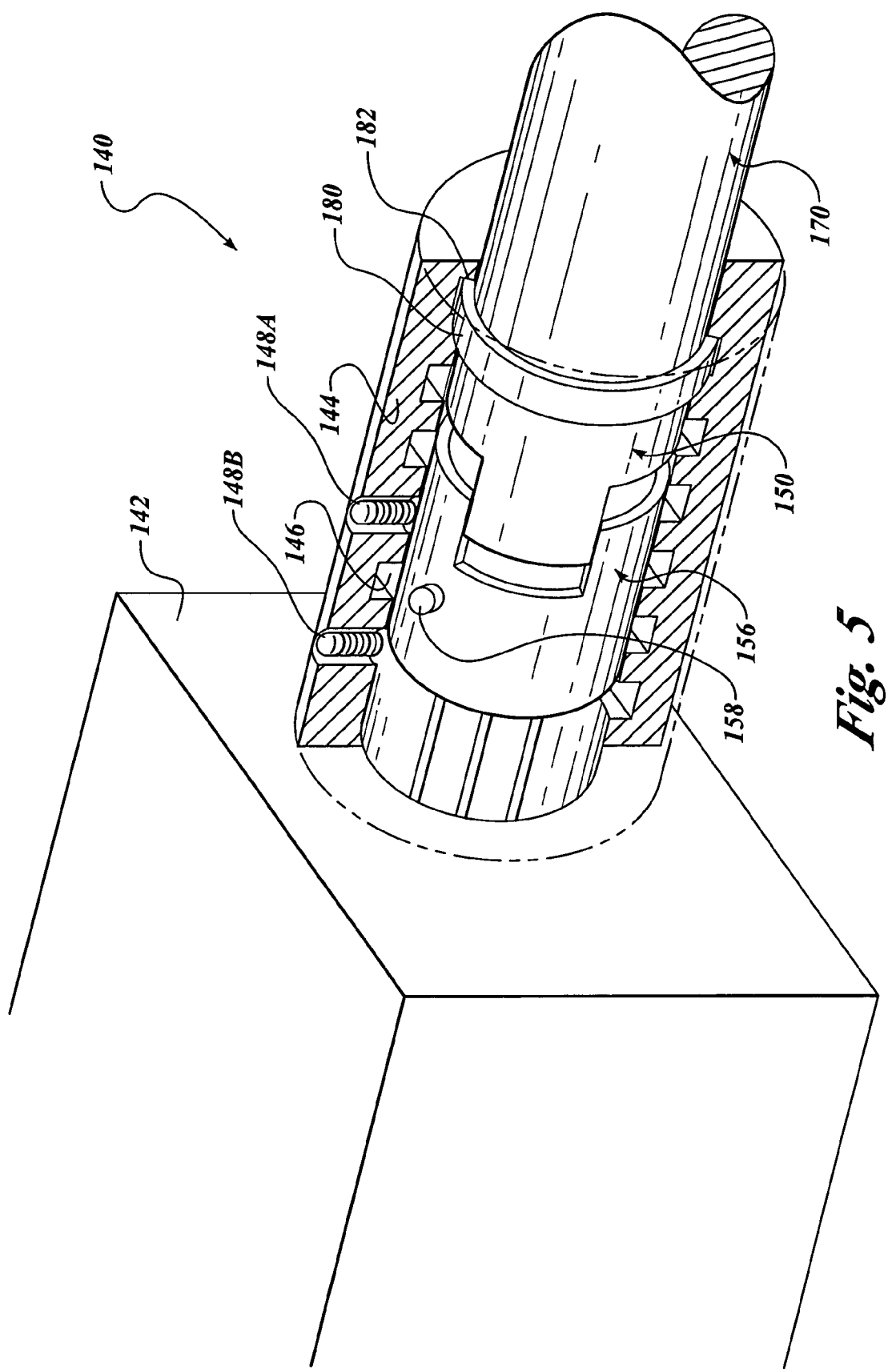
FIG. 5 illustrates another embodiment of a selectively rotatable shaft coupler that maintains the effective length of an endoscope shaft during rotation, in accordance with another embodiment of the present invention.

In another embodiment, the present invention provides a selectively rotatable shaft coupler that attaches an endoscope shaft to a housing and maintains the effective length of the endoscope shaft during rotation. FIG. 5 is a partial cutaway view of an embodiment of a selectively rotatable shaft coupler 140 that extends from, or is attached to, for example, an anchor point such as an object 142. As shown, an internally threaded collar 144 extends from and is integrally formed with, or is attached to, the object 142. One end of an endoscope shaft 170 is secured to a first end of a shaft adapter 150. A second end of the shaft adapter 150 has alternating tangs and notches that slidably engage a corresponding set of tangs and notches on a rotary adapter 156. A circular flange 180 on the shaft adapter 150 is rotatably fitted in an annular slot 182 that extends around the interior of the collar 144.

An engagement pin 158 on the rotary adapter 156 rides in the threads 146 of the collar 144 and causes the rotary adapter 156 to move axially in and out of the collar 144 during rotation of the endoscope shaft 170. To limit rotation of the shaft, one or more stop elements 148A, 148B extend into the threads 146 of the threaded collar 144, to prevent further rotation of the engagement pin 158. The location of each of the two stop pins 148A, 148B in the threads 146, and the pitch of the threads determines the range of endoscope shaft rotation.

Figure 6:
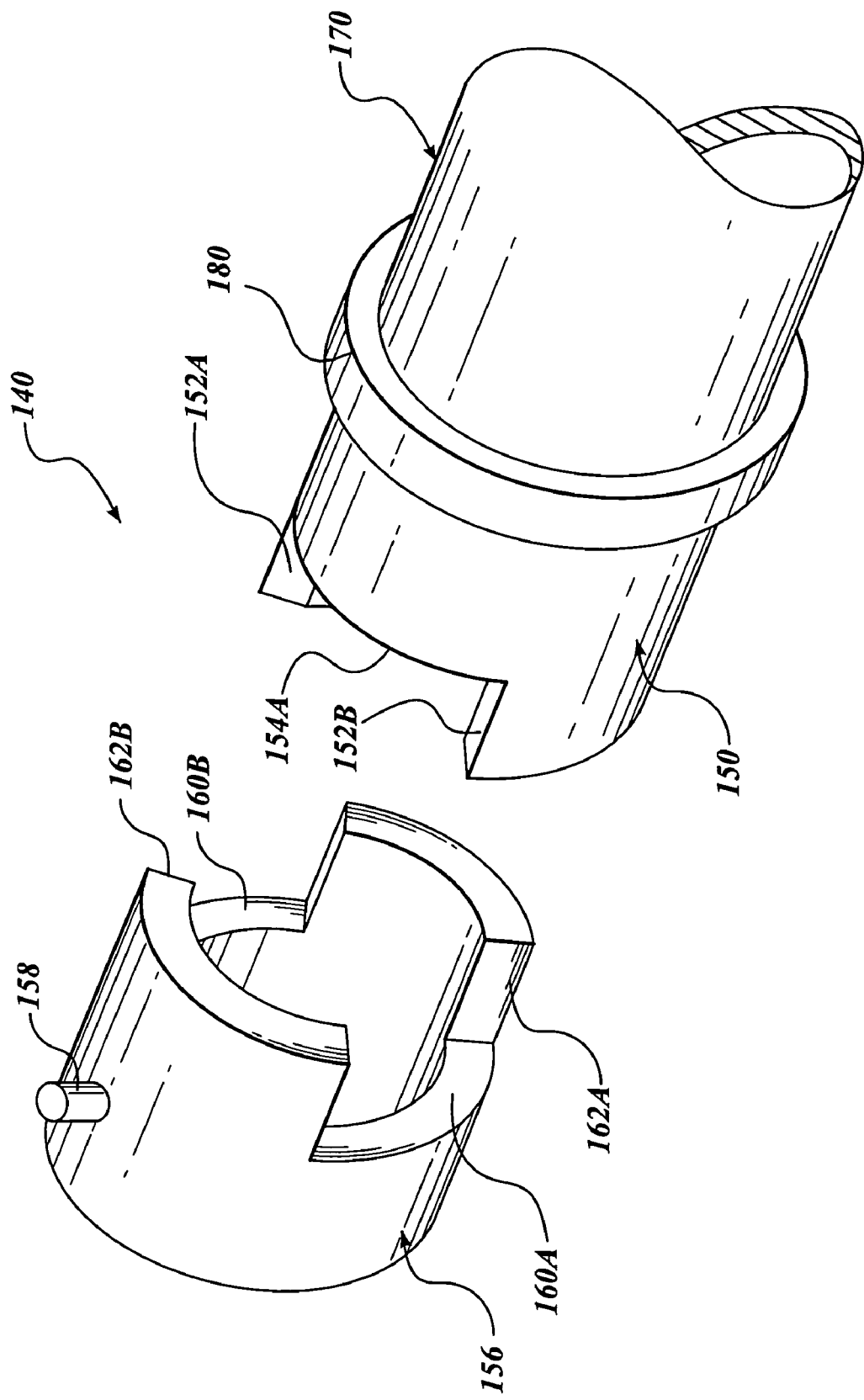
FIG. 6 shows a perspective view of the interface between the tangs and notches on interconnecting members of the shaft adapter shown in FIG. 5.

FIG. 6 illustrates the interlocking elements of the shaft adapter 150 and the rotary adapter 156 in the selectively rotatable shaft coupler 140. As shown, the first end of the shaft adapter 150 is adapted to be secured to the endoscope shaft 170 and the second end has two or more opposing tangs 152A, 152B alternating with two or more opposing notches 154A, 154B. The rotary adapter 156 has a corresponding set of tangs 162A, 162B and notches 160A, 160B which fit within the notches 154A, 154B and tangs 152A, 152B of the shaft adapter 150, respectively. As the rotary adapter 156 is rotated in the threaded collar 144, the rotary adapter 156 and the shaft adapter 150 separate or are forced closer together because the shaft adapter 150 is held within the collar 144 by the circular flange 180 in the annular slot 182. The length of the tangs and notches are chosen to allow continued slideable engagement through the desired range of endoscope shaft rotation.

Referring again to FIG. 5, in operation, the rotation of the endoscope shaft 170 causes the flange 180 on the shaft adapter 150 to rotate in the annular slot 182 in the collar 144. During rotation of the shaft adapter 150, the tangs on the shaft adapter engage in the notches of the rotary adapter 156, causing the rotary adapter 156 to rotate along with the endoscope shaft 170. As the rotary adapter 156 rotates in a first direction (e.g., clockwise), the engagement pin 158 moves along the threads 146 of the threaded collar 144, causing the rotary adapter 156 to move axially toward the object 142 until the engagement pin 158 contacts the stop pin 148B, thereby preventing further clockwise rotation. Similarly, when the rotation is in the counterclockwise direction, the rotary adapter moves away from the object 142 until the stop pin 148A prevents further rotation. Due to the circular flange 180 of the shaft adapter being retained in the annular slot 182, the shaft adapter 150 is not able to move axially in the channel during rotation of the shaft. Therefore, the effective length of the endoscope shaft 170 does not change during rotation. This aspect of the invention advantageously allows the axial position of the endoscope tip to be maintained in the body during rotation. Furthermore, the internal components in the endoscope shaft do not contract or stretch during rotation.

Although the embodiment shown in FIG. 5 uses two stop pins 148A, 148B, it will be appreciated that a single stop pin 148B could be used by limiting the depth of the threads in the collar 144 such that the engagement pin 158 on the rotary adapter 156 cannot ride in the threaded grooves, thereby limiting rotation of the endoscope shaft 170. Alternatively, the depth of travel of the rotary adapter 156 can be selected solely by the depth of the threads 146.

Figure 8A:
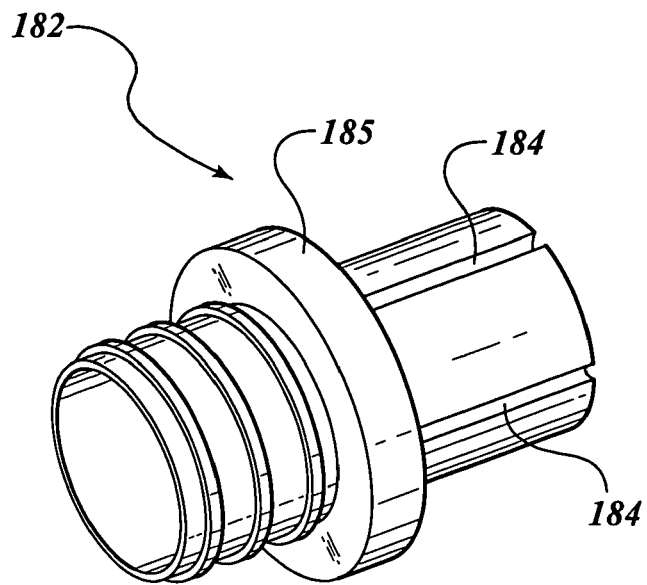
FIG. 8A shows a perspective view of a shaft adapter having grooves along the longitudinal axis in accordance with one embodiment of the present invention.
Figure 8B:
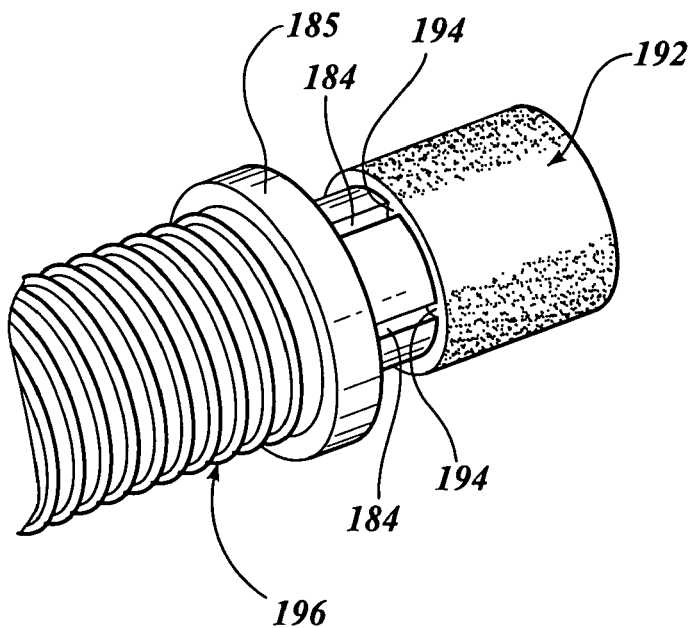
FIG. 8B shows a perspective view of the interface between the shaft adapter having grooves and a rotary adapter having corresponding ribs, in accordance with one embodiment of the present invention.

FIG. 7 is a partial cutaway drawing illustrating an alternative embodiment of a selectively rotatable shaft coupler 180 that attaches an endoscope shaft 196 to an anchor point, such as an object 190. The shaft coupler 180 maintains the effective length of the endoscope shaft 196 during rotation. In the embodiment shown in FIG. 7, a shaft adapter 182 has a set of grooves 184 on an outer surface and extending in the direction that slidably engage a corresponding set of ribs 194 on a rotary adapter 192. An engagement pin 198 on the rotary adapter rides in the threads of the object 190 and a stop 199 at the end thereof prevents further axial movement of the rotary adapter 192, thereby limiting rotation of the shaft 196. The longitudinal grooves 184 on the shaft adapter 182 are best shown in FIG. 8A. FIG. 8B illustrates the rotary adapter 192 with ribs 194 slidably engaged in the grooves 184 on the shaft adapter 182. In the embodiment shown, the endoscope shaft 196 is corrugated to provide additional flexibility in the shaft. A circular flange 185 allows the rotary adapter 182 to rotate in the collar (see FIG. 7), but prevents axial movement of the shaft adapter 182, thereby maintaining the effective length of the endoscope shaft 196 during rotation. The rotatable shaft coupler 180 is preferably assembled by forming the object 190 in two halves that are fitted over the rotary adapter 192 and the shaft adapter 182. Although the embodiment shown in FIGS. 7, 8A, 8B puts the grooves 184 on the shaft adapter 182 and the ribs 194 on the rotary adapter 192, it will be appreciated that the position of the ribs and the grooves could be reversed.

Figure 9:
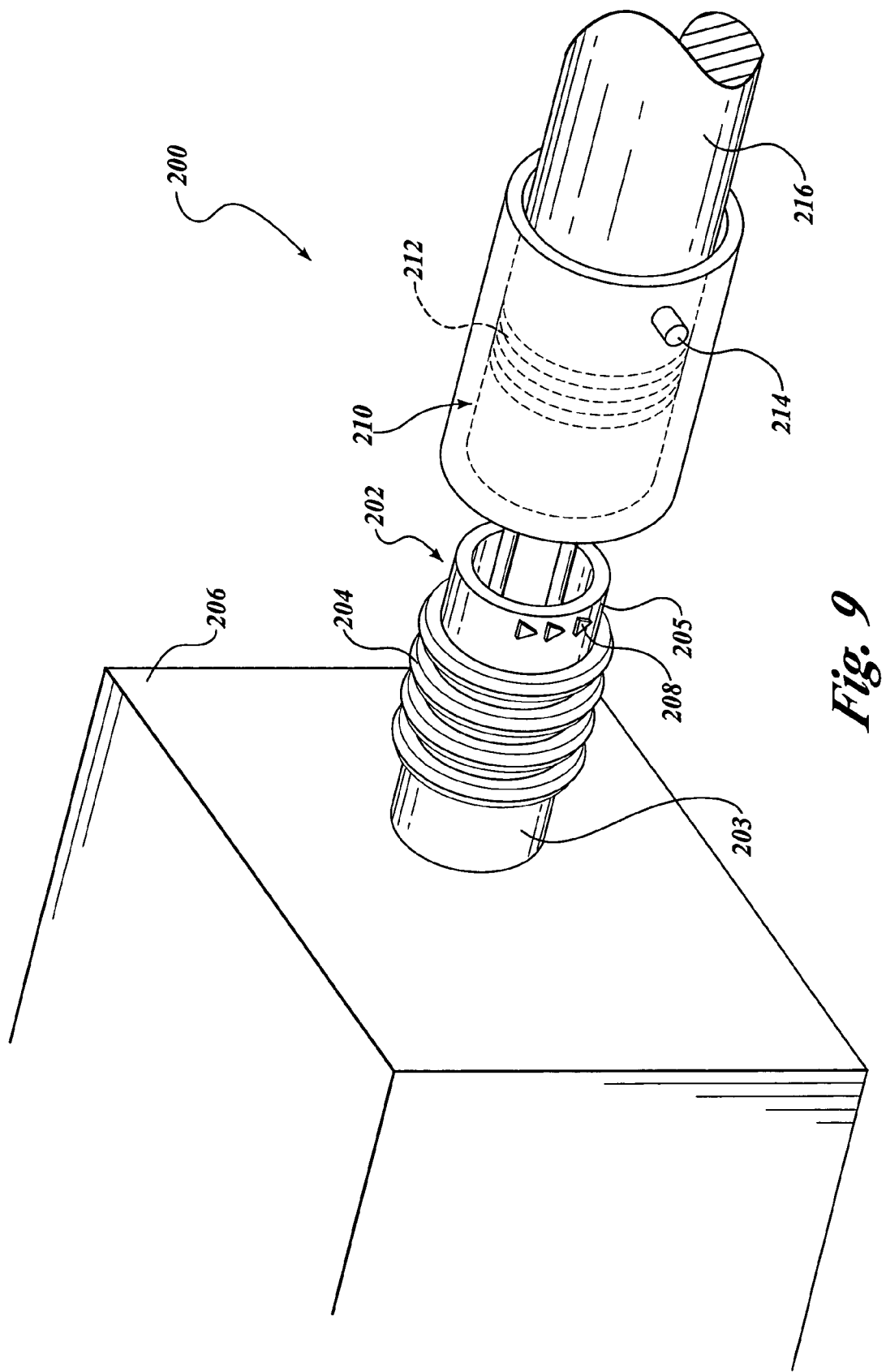
FIG. 9 shows a selectively rotatable shaft coupler having a shaft adapter in accordance with one embodiment of the present invention.

In another embodiment, the present invention provides a selectively rotatable shaft coupler 200 having a shaft adapter with a first end fixed to an anchor point such as a housing or other object, and a second end adapted to rotatably receive an endoscope shaft. As shown in FIG. 9, the shaft coupler 200 comprises a shaft adapter 202 with a first end 203 that is non-rotatably attached to an object 206 and a second end 205 sized to rotatably receive an end of a shaft collar 210. The shaft adapter 202 has a threaded section 204 midway between the first end 203 and the second end 205. Positioned between the threaded section 204 and the second end 205 is a set of ratchets 208 capable of functioning as one-way stop elements, as further described below. The shaft collar 210 is fixedly secured over an end of a shaft 216. The collar 210 has a pawl 214 extending inwardly toward the shaft 216 and located at a position chosen to stop rotation of the shaft 216 if rotated against the ratchets 208. The shaft 216 has a threaded section 212 that allows the collar 210 to be screwed onto the threaded section 204 on the shaft adapter 202. In operation, the collar 210 is secured over the end of the shaft 216. The shaft 216 and the collar 210 are then screwed onto the shaft adapter 202 and the ratchets 208 so that the pawl 214 passes over the ratchet elements 208. Once the threaded section 212 of the shaft 216 is screwed onto the threaded section 204 of the shaft adapter 202, the shaft 216 can be further rotated in a clockwise direction until the end of the shaft 216 and/or collar 210 contacts the wall of the housing 206. Rotation of the shaft 216 in a counterclockwise direction is permitted until the pawl 214 on the collar 210 contacts the one way ratchets 208, thereby preventing further counterclockwise rotation.

Figure 10A:
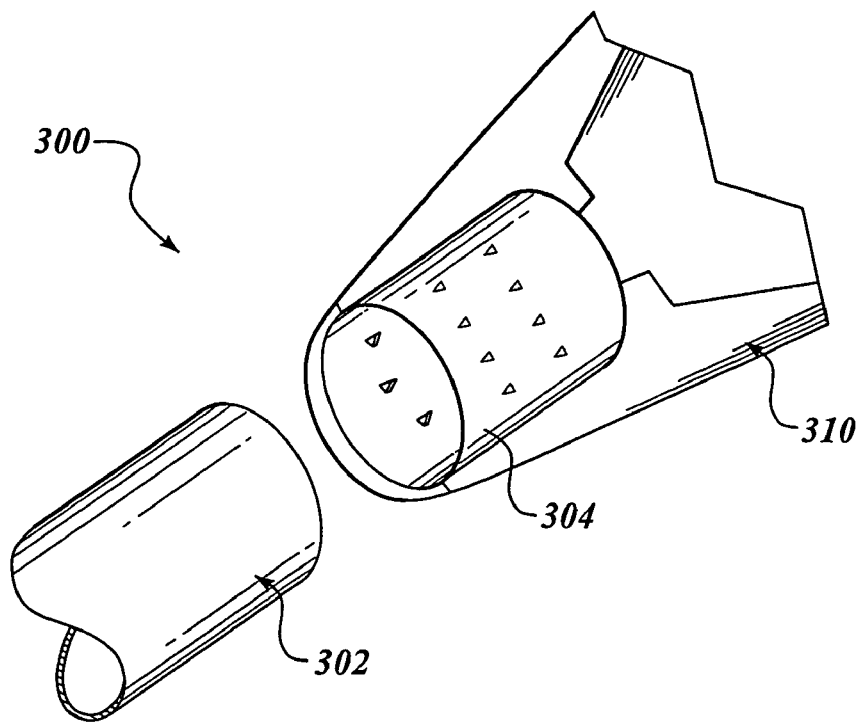
FIG. 10A illustrates a shaft retainer having inwardly and outwardly facing barbs, in accordance with another embodiment of the invention.
Figure 10B:
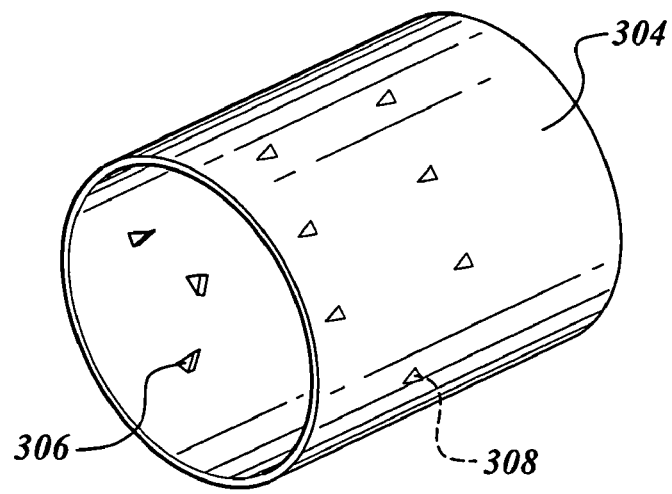
FIG. 10B shows a perspective view of the shaft retainer having inwardly and outwardly facing barbs in accordance with one embodiment of the invention.

In another embodiment, the present invention provides a shaft coupling system for connecting a proximal end of an endoscope shaft 302 to an anchor point such as a housing 310 or other structure without the use of adhesives. A representative embodiment of the shaft coupling system 300 is shown in FIG. 10A. As shown, an endoscope shaft 302 is coupled to the housing 310 via a shaft retainer 304 that is press-fit into the housing 310. As shown more clearly in FIG. 10B, the shaft retainer 304 has a cylindrical hollow shape that is sized to fit into the housing 310. The outer surface of the shaft retainer 304 has a plurality of retention elements, such as, for example, outwardly extending barbs 308 capable of securing the shaft retainer 304 into the housing 310. The inner surface of the shaft retainer body has a plurality of retention elements, such as inwardly extending barbs 306 that are capable of securing the endoscope shaft 302 into the shaft retainer 304. The shaft retainer 304 may additionally have a circular flange (not shown) at one end to ease the insertion of the endoscope shaft 302.

The shaft retainer 304 may be made out of metal and be stamped or molded to form the plurality of retention elements such as inwardly and outwardly extending barbs. The stamped shaft retainer 304 may then be press-fit into the housing 310. In operation, the shaft retainer 304 is slid over the endoscope shaft 302 and is prevented from being pulled off by the barbs 306. The shaft retainer 304 is then inserted into the housing 310 and is retained by the outwardly extending barbs 308.

Figure 11A:
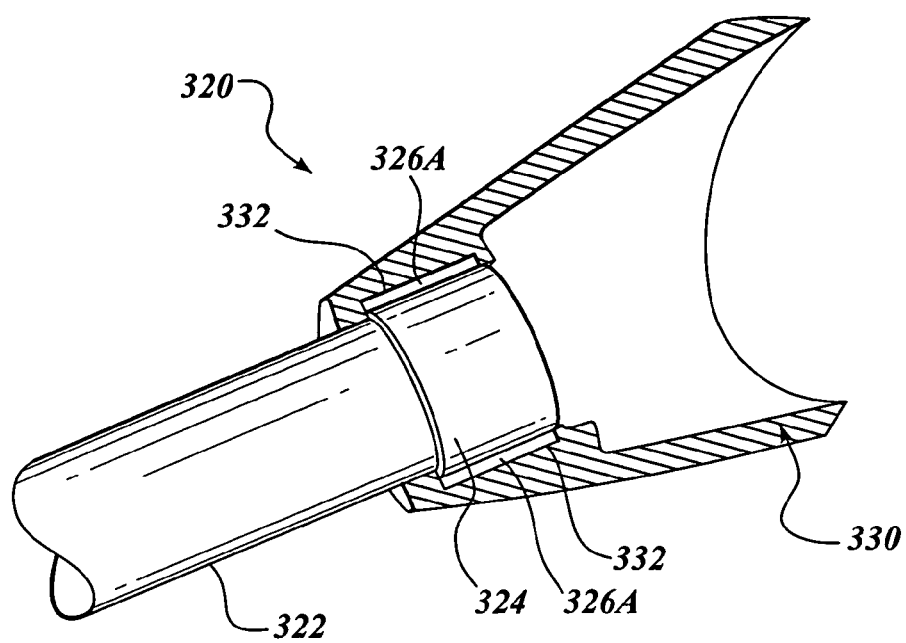
FIG. 11A illustrates an alternative embodiment of a shaft retainer having anti-rotation bosses coupled to a breakout box housing.
Figure 11B:
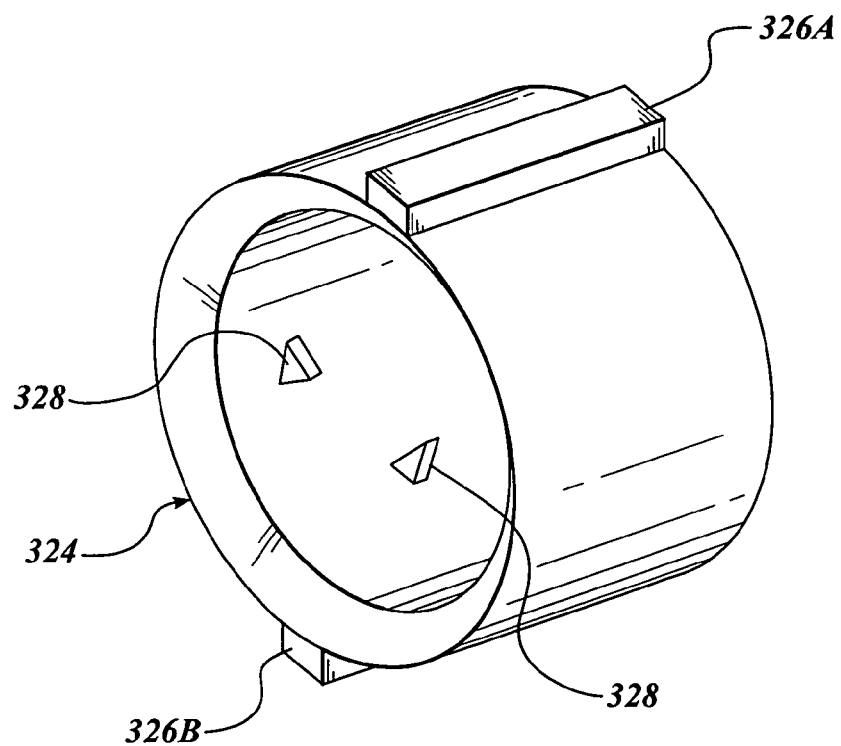
FIG. 11B shows a perspective view of the shaft retainer having anti-rotation bosses in accordance with one embodiment of the invention.

An alternative embodiment of a shaft coupling system 320 is shown in FIG. 11A. In this embodiment, an endoscope shaft 322 is secured in a shaft retainer 324 having one or more anti-rotation bosses 331. The shaft retainer 324 is fitted into a housing 330 having pockets or slots 332 that are sized to receive the one or more anti-rotation bosses 331. In addition, the pockets or slots 332 include radially inwardly extending tabs that engage the bosses so that the shaft retainer is not able to freely rotate in the housing 330. As shown more clearly in FIG. 11B, the shaft retainer 324 has two anti-rotation bosses 326A, 326B that protrude radially outward from the shaft retainer body. The inwardly facing surface of the shaft retainer body comprises a plurality of inwardly extending barbs 328 capable of securing the shaft retainer 324 to the endoscope shaft 322. The shaft retainer 324 with anti-rotation bosses 326A, 326B may be injection molded and fitted onto the proximal end of an endoscope shaft, wherein the inwardly extending barbs 328 secure the endoscope shaft without the need for adhesives or epoxies. The shaft retainer 324 secured to the endoscope shaft 322 may then be assembled with two halves of the housing 330, such that the one or more anti-rotation bosses 326A, 326B are fitted into preformed pockets 332 in the housing. The coupling system 320 thereby allows for a secured connection between the endoscope shaft and a housing without allowing rotation and prevents pull-out of the endoscope shaft and without the need for adhesives or fasteners.

Figure 12:
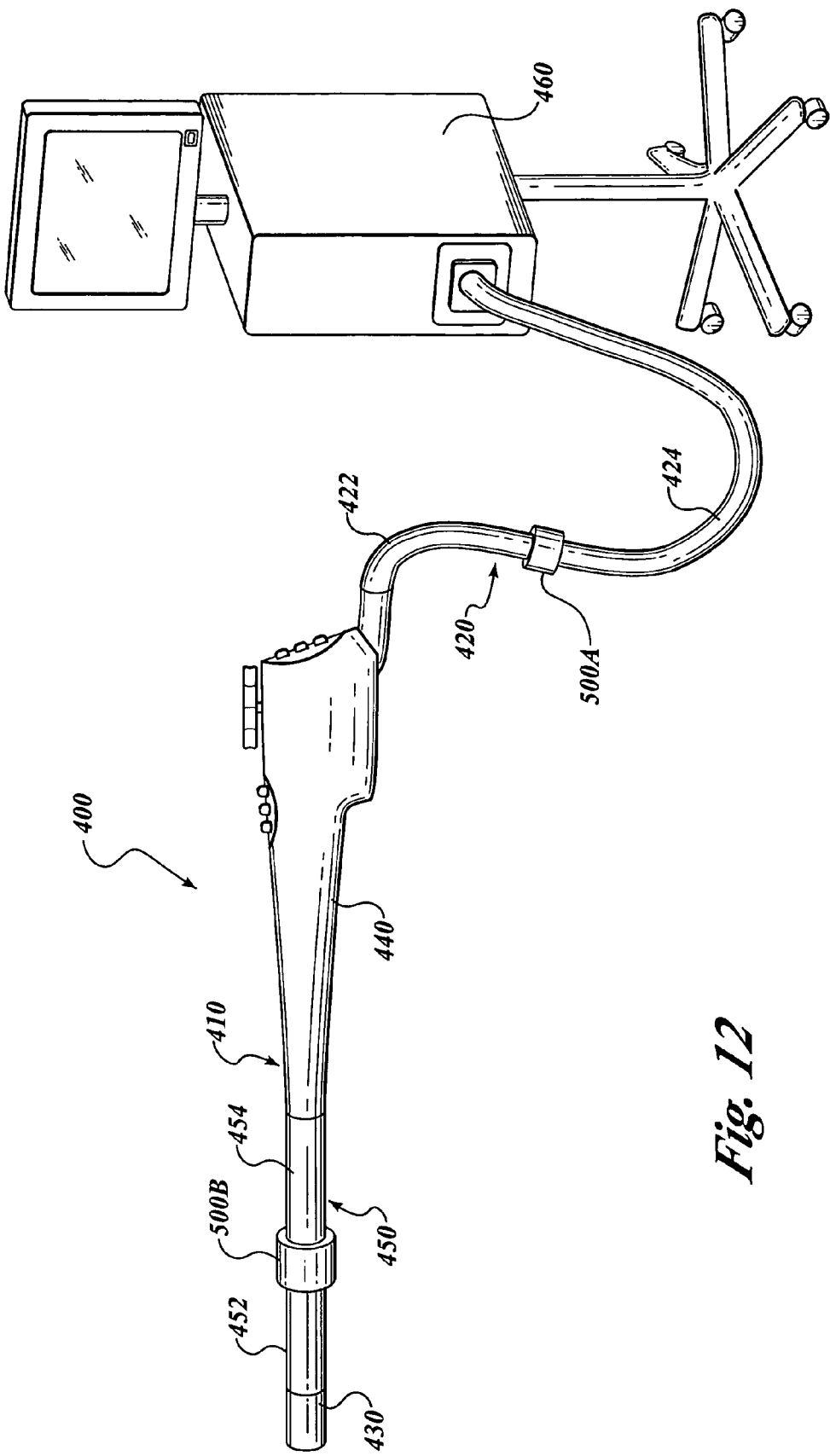
FIG. 12 illustrates an endoscope system that includes a plurality of swivel joints in accordance with another embodiment of the invention.

In another embodiment, the present invention provides an endoscope system 400 comprising one or more selectively rotatable swivel joints 500A, 500B for connecting two segments of a shaft, as shown in FIG. 12. The system 400 includes an endoscope 410 comprising an elongated distal shaft 450 connected to a handle 440. The handle 440 is connected to a control console 460 via a proximal shaft 420. The proximal shaft 420 comprises a first shaft segment 422 and a second shaft segment 424 that are connected via the swivel joint 500A. The distal shaft 450 comprises a first shaft segment 452 and a second shaft segment 454 connected via the swivel joint 500B.

The swivel joints 500A, 500B functionally and rotatably couple a first segment and a second segment of a segmented shaft, as described in more detail below. The swivel joints 500A, 500B may be positioned at any location intermediate the distal end and the proximal end of the distal shaft 450 or the proximal shaft 420. In another embodiment, one or more swivel joints 500A, 500B are positioned at the junction between a shaft and an anchor point, such as a housing or an object. For example, one or more swivel joints 500A, 500B may be positioned between the distal shaft 450 and the handle 440, or at the junction between the handle 440 and the proximal shaft 420, or at the junction between the proximal shaft 420 and the control console 460.

Figure 13:
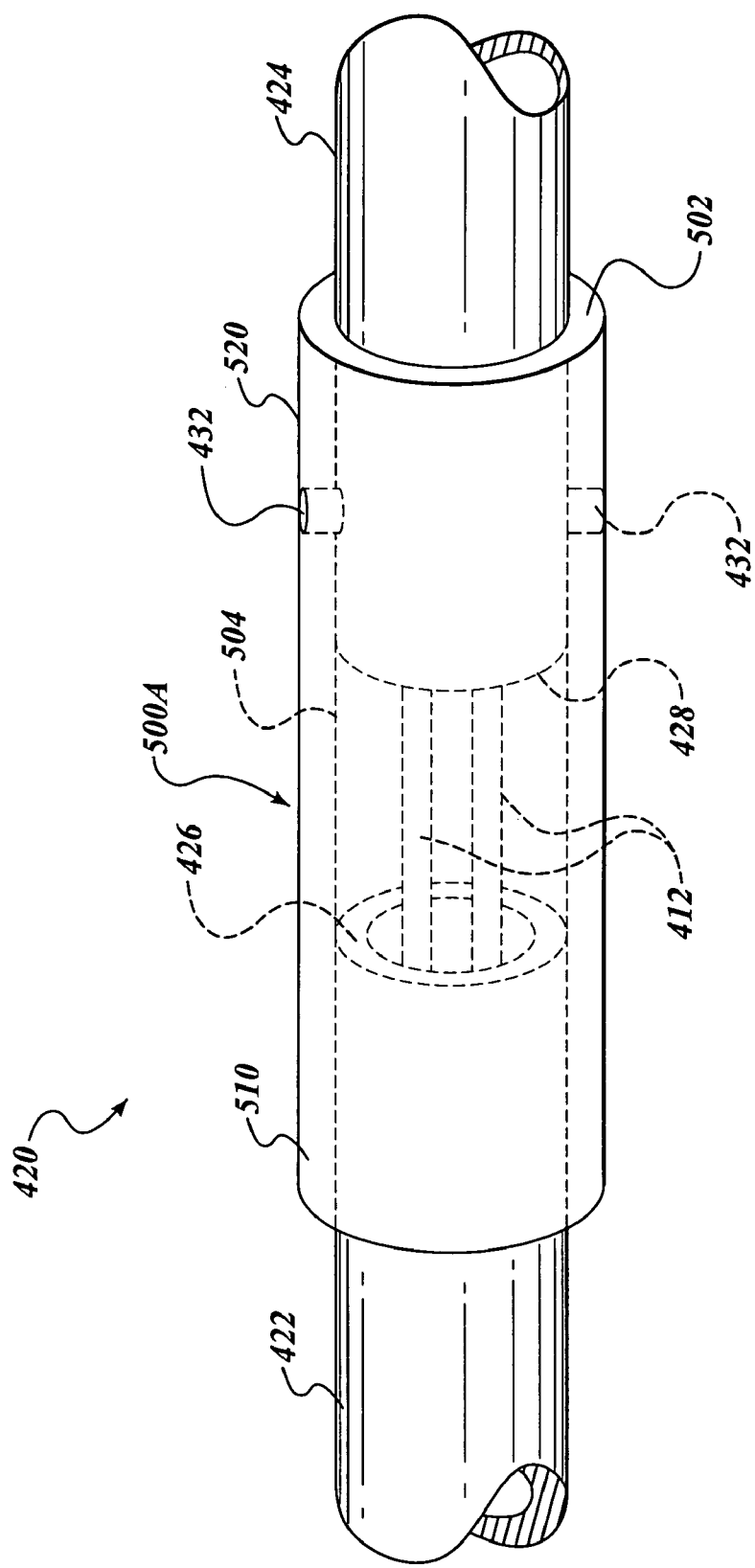
FIG. 13 shows a perspective view of an embodiment of a swivel joint connecting a first shaft segment and a second shaft segment.

FIG. 13 illustrates one embodiment of a swivel joint 500A that rotatably couples a first shaft segment 422 (connected to the handle 440) and a second shaft segment 424 (connected to the control console 460) of the proximal shaft 420. As shown, the swivel joint 500A comprises a tubular housing 502 with a first end 510 adapted to rotatably receive the end 426 of the first shaft segment 422. The tubular housing 502 further includes a second end 520 adapted to fixedly receive an end 428 of the second shaft segment 424. As shown, the swivel joint tubular housing 502 has a central hollow lumen 504 through which lumens 412, electrical wires and other elements of the proximal shaft 420, are passed to allow electrical, irrigation and aspiration connections to extend from the control console 460 to the endoscope 410. The housing 502 of the swivel joint 500A forms a protective cuff that overlaps, surrounds and rotatably couples a first end 426 of the first shaft segment 422 with a second end 428 of the second shaft segment 424 of the proximal shaft 420.

Figure 14:
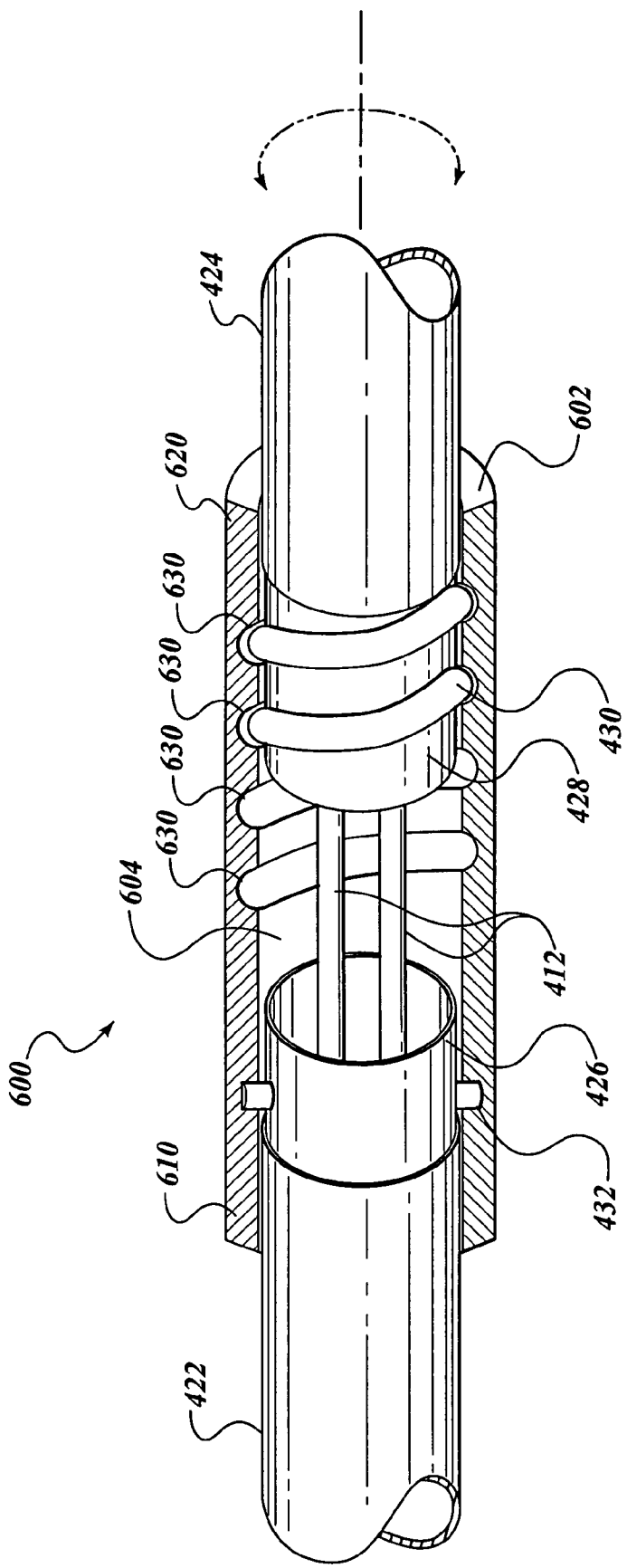
FIG. 14 shows a partial cutaway view of an embodiment of a swivel joint comprising a first end adapted to rotatably receive a shaft segment and a second end adapted to fixedly receive a second shaft segment.

FIG. 14 is a partial cutaway view of an embodiment of a limited rotation swivel joint 600 that rotatably connects the first shaft segment 422 and the second shaft segment 424 of the proximal shaft 420. As shown, the swivel joint 600 comprises a tubular housing 602 with a first end 610 adapted to fixedly receive an end 426 of the first shaft segment 422. The end 426 of the first shaft segment 422 may be secured inside the housing 602 by a variety of means such as an adhesive, and/or with one or more attachment structure(s) 432. The attachment structure(s) 432 may be any suitable structure capable of securing the shaft end 426 in the tubular housing 602, such as one or more pins or a lip that is adhesively secured in a cooperating slot within the housing 602, one or more barbs extending outward from the housing 602, and the like.

With continued reference to FIG. 14, the tubular housing 602 further comprises a second end 620 adapted to rotatably receive the end 428 of the second shaft segment 424. As shown, the interior of the second end 620 of the housing 602 has a threaded section 630 into which a set of cooperating threads 430 on the end 428 of the shaft segment 424 are inserted. The threads of the threaded section 630 have a size and pitch selected to allow the desired amount of limited rotation of the second shaft segment 424 in the tubular housing 602. For example, the threads can be cut or molded to allow between one to four or more full rotations of the shaft 424. In the embodiment shown, the threaded section 630 does not extend to the end of the tubular housing 602 such that the shaft segment 424 cannot be disengaged from the tubular housing 602. In this embodiment, the tubular housing 602 can be formed of two molded sections that are adhesively secured over the ends of the shafts to assemble the swivel joint 600.

Although the embodiment shown in FIG. 14 shows the threaded section 630 of the tubular housing 602 rotatably coupled with the shaft segment 424 and the shaft segment 422 as being fixedly secured to the housing 602, it will be appreciated that the position of the shaft segments 422, 424 in the tubular housing 602 could be reversed.

In operation, rotation of the shaft segment 424 in a first direction (e.g., clockwise) causes incremental axial movement of the end 428 of the shaft 424 towards the center of the tubular housing 602 until the threads 430 on the shaft 424 reach the end of the threaded section 630 and is stopped adjacent to the end 426 of the first shaft segment 422. Therefore, as a physician applies torque to the endoscope 410 during insertion into the patient, the swivel joint 600 takes up any loops that may be formed by the physician.

Figure 15:
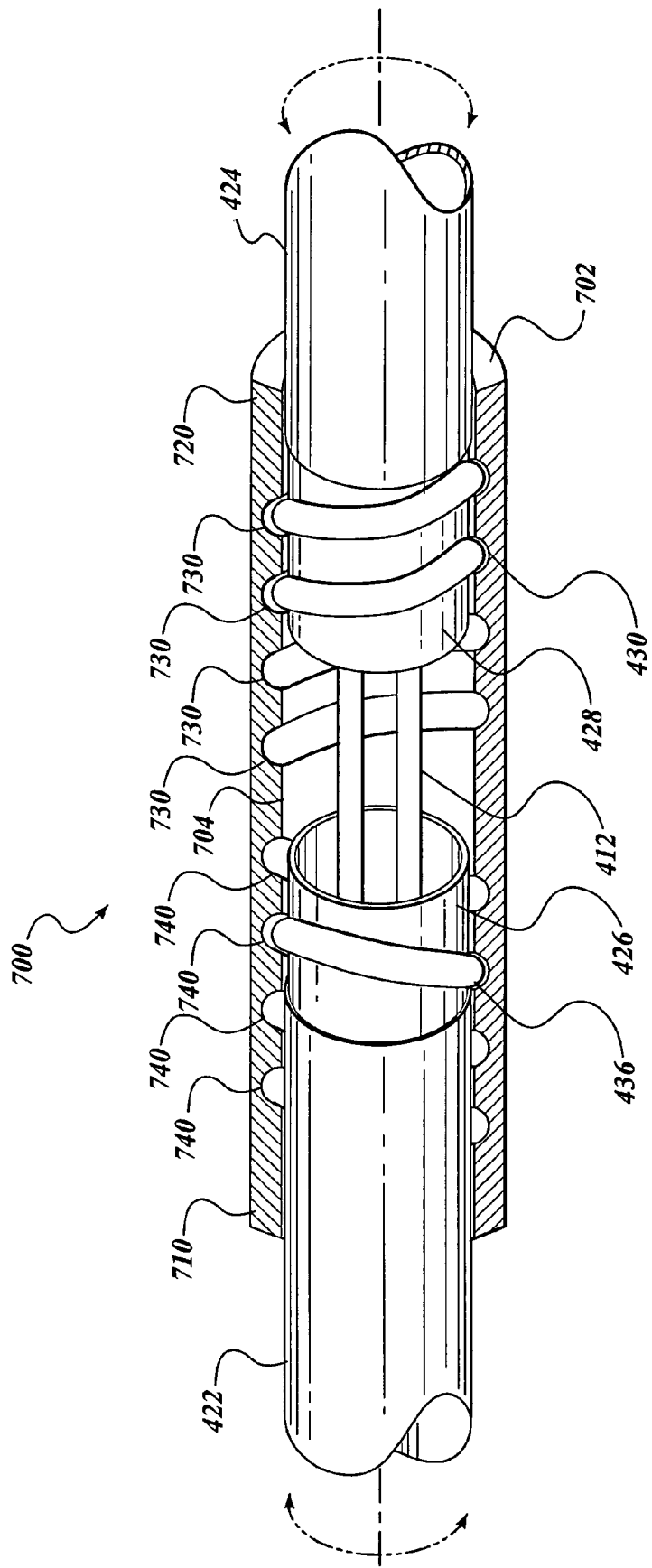
FIG. 15 shows a partial cutaway view of another embodiment of a swivel joint comprising a first end and a second end adapted to rotatably receive a first and a second shaft segment.

FIG. 15 is a partial cutaway of another embodiment of a swivel joint 700 capable of rotatably connecting the first shaft segment 422 and the second segment 424 of the proximal shaft 420. As shown, the swivel joint 700 comprises a tubular housing 702 with a first end 710 adapted to rotatably receive the end 426 of the first shaft segment 422. As shown, the first end 710 of the housing 702 comprises a threaded section 740 into which a corresponding threaded section 436 on the first shaft segment 422 is inserted. The tubular housing 702 includes a second end 720 adapted to rotatably receive the end 428 of the second shaft segment 424. The second end 720 of the housing 702 also includes a threaded section 730 into which a corresponding threaded section 430 on the second shaft segment 424 is inserted.

In one embodiment of the swivel joint 700, the threads in the threaded section 730 at one end of the tubular housing 702 are formed in an opposite direction from the threads in the threaded section 740 at the other end of the tubular housing 702 (e.g., threaded section 730 is threaded in a clockwise direction and threaded section 740 is threaded in a counterclockwise direction). Similarly, each shaft end 426, 428 includes threaded sections 436, 430 with threads formed in a direction corresponding to the threaded sections 730, 740, such that the shafts move in opposite directions within the tubular housing when rotated in the same direction. For example, in the embodiment shown, rotating the shaft 424 in the clockwise direction advances the end of the shaft 428 toward the center of the tubular housing 702. The shaft 424 advances until it reaches the end of the thread 730. Further clockwise rotation of the shaft 424 in the clockwise direction causes the end of the shaft 422 to move away from the center of the tubular housing 702. Therefore, in the example shown, it is possible to get eight revolutions of the shaft with only 4×360° threads for each shaft.

As described above, each threaded section 730, 740 within the tubular housing 702 is designed to include a number of threads of a size and pitch to allow the desired amount of limited rotation of the shaft segments 422, 424. For example, each end of the swivel joint may allow between one full to four full rotations, thereby resulting in a total rotational range of the proximal shaft 420 from two full rotations up to eight rotations.

Figure 16:
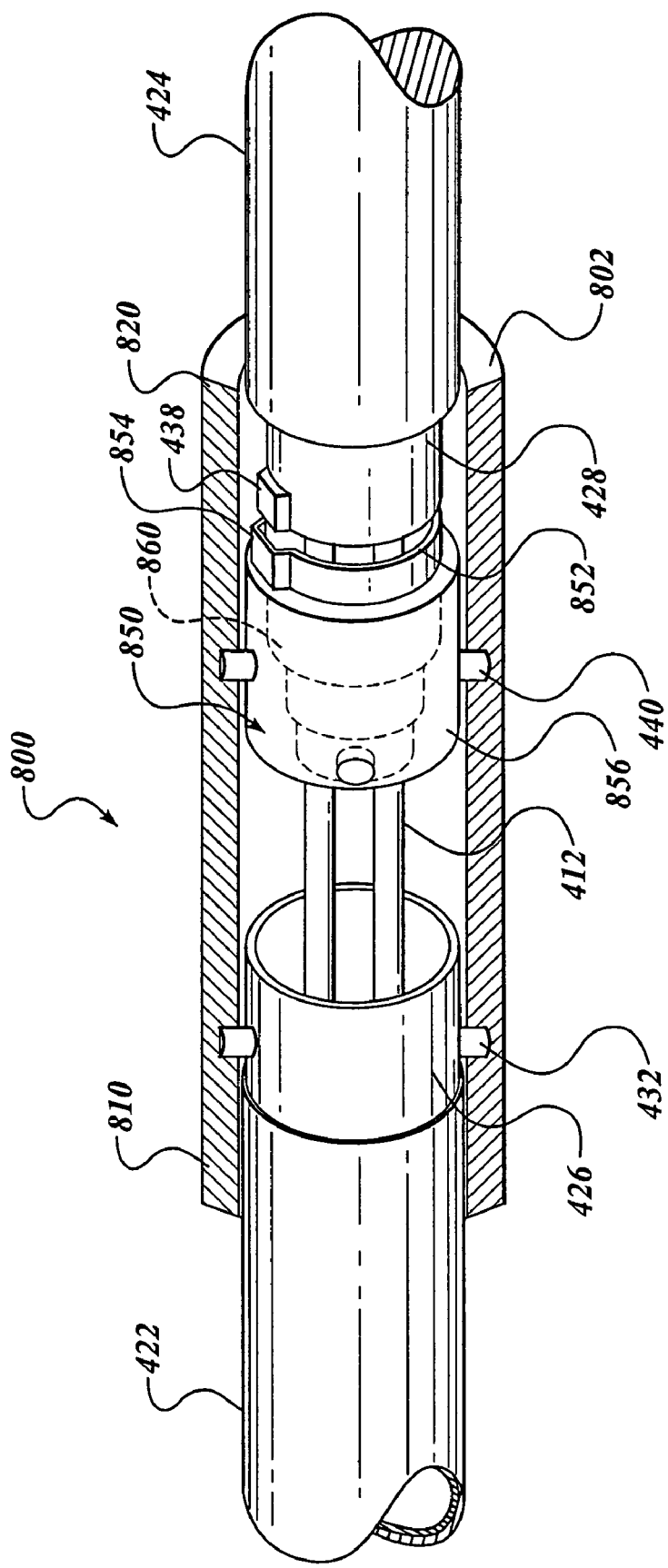
FIG. 16 shows a partial cutaway view of another embodiment of a swivel joint comprising a first end including a swivel device.

FIG. 16 is a partial cutaway view of another embodiment of a swivel joint 800 capable of rotatably connecting the first shaft segment 422 and the second shaft segment 426 of the proximal shaft 420. As shown, the swivel joint 800 comprises a tubular housing 802 with a first end 810 adapted to fixedly receive the end 426 of the first shaft segment 422. The tubular housing 802 includes a second end 820 adapted to rotatably receive the end 428 of the second shaft segment 424. As shown, the second end 820 of the housing 802 includes a swivel device 850 secured therein with an attachment element 440. The swivel device 850 comprises a housing 856 surrounding a set of nested, concentric, cylinders 860, such as from two to four or more nested cylinders. Each cylinder in the set 860 includes a central hollow lumen (hidden from view) through which internal elements of the endoscope shaft may be passed. As shown in FIG. 16, innermost cylinder in the set is fixedly attached to the housing 856 of the swivel device 850. The remaining cylinders are rotatably secured in the housing 856. The outermost cylinder 852 in the set includes at least one slot 854 to receive at least one corresponding tab 438 on the end of the second shaft segment 428. Each nested cylinder has a stop element thereon capable of limiting the rotation of an adjacent cylinder such that the nested cylinders function to allow limited rotation of the shaft segment 424.

The various embodiments of the swivel joints (500, 600, 700, and 800) may be made out of any suitable material such as metal or moldable plastic. The swivel joint tubular housing (602, 702 and 802) may be formed into two separate molded components that snap together around the ends 426, 428 of the proximal shaft segments. The proximal shaft 420 comprising the shaft segment 422 and the shaft segment 424 connected via the swivel joints 500, 600, 700 or 800 may be packaged as a preformed unit that can be removably attached to a housing, such as the handle 440, or to any desired object with any suitable connection means.

While embodiments of the invention have been illustrated and described, it will be appreciated that various changes can be made therein without departing from the scope of the invention. It is therefore intended that the scope of the invention be determined from the following claims and equivalents thereof.

The embodiments of the invention in which an exclusive property or privilege is claimed are defined as follows:

1. A system for rotatably coupling a first segment of an endoscope shaft to a second segment of an endoscope shaft, the system comprising:
   (i) an endoscope shaft comprising a proximal end and a distal end and one or more internal components of the endoscope passing therethrough; wherein the shaft is formed into a first segment having a first threaded end and a second segment having a second threaded end; and
   (ii) a joint having a housing with a first end and a second end secured, respectively, to the first threaded end of the first segment and the second threaded end of the second segment, each of the first and second ends of the housing including a threaded bore adapted to rotatably receive a corresponding one of the first threaded end of the first segment and the second threaded end of the second segment, and wherein each of the threaded bores of the first and second ends of the housing includes more threads than present on a corresponding one of the first threaded end of the first segment and the second threaded end of the second segment, wherein the first and second ends of the housing are configured such that they do not rotate relative to each other, and wherein during operation of the system, at least one of the first and second segments of the shaft is rotatable in and with respect to the housing;
   wherein a first amount of rotation of the second segment in a first direction causes the second segment to move towards the first segment, and wherein further rotation of the second segment in the first direction causes the first segment to move away from the second segment; and
   wherein a thread of the threaded bore of the first end of the housing extends a distance along the bore such that the thread does not extend to either the first end or the second end of the housing.

2. The system of claim 1, wherein each of the first and second ends includes only one continuous thread.

3. The system of claim 1, wherein the threads of the threaded bore included in the first end are oriented in a direction opposite from the threads of the threaded bore included in the second end.

4. The system of claim 1, wherein the one or more internal components of the endoscope include at least one of an illumination element and an imaging element.

5. A system for rotatably coupling segments of an endoscope shaft, the system comprising:
   a first housing have a first end and a second end, a first segment of the endoscope shaft being rotatably secured to the first end of the first housing and a second segment of the endoscope shaft being rotatably secured to the second end of the first housing, each of the first and second ends of the first housing including a threaded bore adapted to rotatably receive a corresponding one of a first threaded end of the first segment and a second threaded end of the second segment, wherein each of the first and second segments of the endoscope shaft includes only one continuous thread;
   wherein the first and second ends of the first housing are configured such that they do not rotate relative to each other; and
   wherein a first amount of rotation of the second segment in a first direction causes the second segment to move towards the first segment, and wherein further rotation of the second segment in the first direction causes the first segment to move away from the second segment; and
   wherein a thread of the threaded bore of the first end of the first housing extends a distance along the bore such that the thread does not extend to either the first end or the second end of the first housing.

6. The system of claim 5, wherein the first housing is configured as an integral, unitary piece of material.

7. The system of claim 6, wherein the first housing is tubular.

8. The system of claim 5, wherein the thread of the threaded bore of the first end of the first housing is oriented in an opposite direction as a thread of the threaded bore of the second end of the first housing.

9. The system of claim 5, wherein the longitudinal length of the thread of the threaded bore of the first end of the first housing and the longitudinal length of a thread of the threaded bore of the second end of the first housing are selected such that the first and second segments of the endoscope shaft are permitted to travel along a length of the first housing, and wherein respective ends of the threads on the threaded bore of the first and second ends of the first housing limit further travel of the first and second segments of the endoscope shaft along the length of the first housing.

10. The system of claim 5, further including a second housing having a first end and a second end, wherein a third segment of the endoscope shaft is configured to be rotatably secured to the first end of the second housing and a fourth segment of the endoscope shaft is configured to be rotatably secured to the second end of the second housing.

11. The system of claim 10, wherein a proximal most end of the first segment of the endoscope shaft is configured to be connected to a control console, and a distal most end of the first segment of the endoscope shaft is configured to be rotatably secured to the first end of the first housing.

12. The system of claim 11, wherein a proximal most end of the second segment of the endoscope shaft is configured to be rotatably secured to the second end of the first housing, and a distal most end of the second segment of the endoscope shaft is configured to be connected to a proximal most end of an endoscope handle.

13. The system of claim 12, wherein a proximal most end of the third segment of the endoscope shaft is configured to be connected to a distal most end of the endoscope handle, and a distal most end of the third segment of the endoscope shaft is configured to be rotatably secured to the first end of the second housing.

14. The system of claim 13, wherein a proximal most end of the fourth segment of the endoscope shaft is configured to be rotatably secured to the second end of the second housing, and a distal most end of the fourth segment of the endoscope shaft is configured to be received within a body.

15. The system of claim 12, wherein the first end of the second housing includes a threaded bore having a thread configured to receive an external thread of the third segment of the endoscope shaft, and wherein the second end of the second housing includes a threaded bore having a thread configured to receive an external thread of the fourth segment of the endoscope shaft.

16. The system of claim 5, wherein the endoscope shaft is configured to pass one or more internal components of the endoscope therethough.

17. The system of claim 5, wherein each of the threaded bores of the first and second ends of the first housing includes more threads than present on a corresponding one of the first threaded end of the first segment and the second threaded end of the second segment.

* * * * *